US012539375B2

(12) United States Patent
Stuart et al.

(10) Patent No.: US 12,539,375 B2
(45) Date of Patent: Feb. 3, 2026

(54) MEDICAMENT DISPENSER FOR HOLDING ELONGATE FORM MEDICAMENT CARRIER AND METHOD OF ASSEMBLING THEREOF

(71) Applicant: MERXIN LTD, King's Lynn (GB)

(72) Inventors: Adam Stuart, Norfolk (GB); Stephen Howgill, Leicestershire (GB)

(73) Assignee: MERXIN LTD, King's Lynn (GB)

( * ) Notice: Subject to any disclaimer, the term of this patent is extended or adjusted under 35 U.S.C. 154(b) by 0 days.

(21) Appl. No.: 18/713,267

(22) PCT Filed: Nov. 28, 2022

(86) PCT No.: PCT/IB2022/061471

§ 371 (c)(1),
(2) Date: May 24, 2024

(87) PCT Pub. No.: WO2023/095084

PCT Pub. Date: Jun. 1, 2023

(65) Prior Publication Data

US 2025/0018134 A1 Jan. 16, 2025

(30) Foreign Application Priority Data

Nov. 29, 2021 (GB) ..................................... 2117176

(51) Int. Cl.
*A61M 15/00* (2006.01)

(52) U.S. Cl.
CPC .... *A61M 15/0051* (2014.02); *A61M 15/0043* (2014.02); *A61M 15/0045* (2013.01);
(Continued)

(58) Field of Classification Search
CPC .......... A61M 15/0051; A61M 15/0055; A61M 15/008; A61M 15/0043–0045
See application file for complete search history.

(56) References Cited

U.S. PATENT DOCUMENTS 1,977,458 A * 10/1934 Stargardter ............... F16F 1/10 267/156
2006/0163269 A1* 7/2006 Anderson ......... A61M 15/0045 221/72
(Continued)

FOREIGN PATENT DOCUMENTS

CN 101128234 A * 2/2008 ........ A61M 15/0055
CN 101384289 A 3/2009
(Continued)

OTHER PUBLICATIONS

Intellectual Property Office, Examination Report and Notification of Intention to Grant under Section 18(4); Application No. GB2117176.4, dated Feb. 7, 2024, 2 pages.
(Continued)

*Primary Examiner* — Tu A Vo
(74) *Attorney, Agent, or Firm* — Ziegler IP Law Group, LLC.

(57) ABSTRACT

A medicament dispenser, and a method of assembling a medicament dispenser, for holding at least one elongate form medicament carrier having blister and lid elongate sheets enclosing multiple distinct medicament dose portions therebetween. The medicament dispenser has a dispensing mechanism which is adapted to operate, upon each actuation thereof, to dispense medicament active from the medicament dose portion. Moreover, the mechanism has at least one power spring mechanism for winding the lid elongate sheet, wherein the at least one power spring mechanism has at least one spring having an inner end about which the spring unwinds, and at least one shaft at which the inner end of at least one spring is secured. Furthermore, the power spring mechanism tensions and peels a segment of lid elongate sheet peeled from a corresponding segment of
(Continued)

blister elongate sheet upon each actuation of the medicament dispenser.

18 Claims, 10 Drawing Sheets

(52) U.S. Cl.
CPC ...... *A61M 15/0055* (2014.02); *A61M 15/008* (2014.02); *A61M 15/0003* (2014.02); *A61M 15/0071* (2014.02); *A61M 2202/064* (2013.01); *A61M 2205/52* (2013.01); *A61M 2205/8206* (2013.01); *A61M 2207/00* (2013.01)

(56) References Cited

U.S. PATENT DOCUMENTS

| | | | | |
|---|---|---|---|---|
| 2006/0196504 A1* | 9/2006 | Augustyn | A61M 15/0045 128/203.15 |
| 2010/0012119 A1* | 1/2010 | Sallak | A61M 15/0036 128/203.15 |
| 2010/0229856 A1* | 9/2010 | Von Brunn | A61M 15/0055 128/200.23 |
| 2011/0114088 A1* | 5/2011 | Eason | A61M 15/0036 128/200.21 |
| 2012/0292336 A1* | 11/2012 | Jones | A61M 15/0045 221/25 |
| 2017/0224939 A1* | 8/2017 | Anderson | A61M 15/08 |
| 2021/0085897 A1* | 3/2021 | Gupta | A61M 15/0026 |
| 2021/0386945 A1* | 12/2021 | Ahern | A61M 15/0051 |

FOREIGN PATENT DOCUMENTS

| | | | |
|---|---|---|---|
| EP | 1786498 | A1 | 5/2007 |
| FR | 2918353 | A1 | 1/2009 |
| GB | 2613196 | A | 5/2023 |
| WO | 2005014089 | A1 | 2/2005 |
| WO | 2006018261 | A1 | 2/2006 |
| WO | 2008058964 | A2 | 5/2008 |

OTHER PUBLICATIONS

Intellectual Property Office, Patent Acts 1977: Search Report under Section 17; Application No. GB2117176.4, Dated Apr. 26, 2022, 4 pages.

European Patent Office, International Search Report, Application No. PCT/IB2022/061471, mailed Mar. 23, 2023, 3 pages.

United Kingdom Intellectual Property Office, Report Under Section 15A, Application No. GB2117176.4, mailed Dec. 1, 2021, 2 pages.

United Kingdom Intellectual Property Office, Notice of Publication, Application No. GB2117176.4, mailed May 2, 2023, 2 pages.

United Kingdom Intellectual Property Office, Notification of Grant, Application No. GB2613196, Apr. 30, 2024, 2 pages.

* cited by examiner

200

MEDICAMENT DISPENSER FOR HOLDING ELONGATE FORM MEDICAMENT CARRIER AND METHOD OF ASSEMBLING THEREOF

TECHNICAL FIELD

The present disclosure relates generally to a medicament dispenser for releasing medicament doses; and more specifically, to medicament dispensers for holding elongate form medicament carriers. The present disclosure also relates to methods of assembling the medicament dispensers.

BACKGROUND

Conventionally, dry powder inhalation (DPI) devices are employed for dispensing powder form doses. One type of DPI device administers doses by means of elongate form carriers, such as blister strips, containing a number of discrete doses of medicament in powder form. Notably, specific design of the elongate form carrier (i.e., an elongate lid sheet or film sealing a blister sheet comprising blisters having or containing medicaments) prevents the doses from contamination or degradation by moisture absorption. One sub-type of these devices releases a dose by puncturing the blister and scouring the contents with an airflow generated by the patient. In another sub-type, the lid sheet is peeled away from the blister sheet to expose a dose, again with the contents scoured with an airflow generated by the patient. In order to release the doses from the blisters of this sub-type of device, the lid sheet must be pulled taut and separated from the blister sheet. If the lid sheet is not held taut during peeling, it could become loose, or become out of synchronisation with the dispensing mechanism, resulting in a failed dosing. However, if the lid sheet is held too tightly it could stretch, become loose, break or release the dose too early. These factors may also contribute to an increase in the tendency of mechanical failure for such medicament dispensers. It is therefore critical to ensure the correct handling of lid sheet tensioning during inhaler actuation.

One way of controlling tension of the elongate sheets uses a blister sheet take-up spool and a lid sheet take-up capstan and flexible spring blades to maintain tension on the lid sheet. Operatively, the flexible spring arms are compressed as more lid sheet is spooled onto the capstan. Moreover, said compression is supposed to allow for a constant outer take-up capstan diameter throughout usage of the inhaler device. However, such a property relies on a balancing of the tensions in the unwound used sheet and the flexible spring arms while this sheet and the arms are increasingly separated by windings of used sheet. Furthermore, compression of a plastic component (the flexible spring arms) is maintained for an extended period. If the flexible spring arms do not compress enough, it may result in over-advancement of the lid sheet. Moreover, if the tension created by the capstan is too high the lid sheet might stretch, thus losing tension and cause the sheet to fracture, or pull too far during an actuation, thereby exposing the medicament for the next actuation too early as well as exposing the medicament to atmospheric conditions. Additionally, if the flexible spring arms weaken, some tension in the lid sheet will be lost and the mechanism may jam.

In another disclosure (EP1786498A1), a torsion spring of a sheet driver acts to compensate for any increase in the diameter of the effective winding surface of a fixed-diameter hub during winding of sheet thereabout. Provided at a base of the sheet driver, there is a drive surface for receipt of drive to rotate the base about the rotational axis. A first leg receiver of the base receives a first spring leg of the torsion spring and a second leg receiver of the hub receives a second spring leg of the torsion spring such that relative rotation of the base and the hub results in tensioning of the torsion spring. As lid sheet winds up around the hub the effective winding surface increases and the torsion spring acts such as to compensate for that increase.

In another device of the first sub-type, in which a blister is punctured, a spring is used in a receiver element for taking up used sheet. In such a fluid dispensing device the used elongate carrier is coiled onto a receiver element. However, such a device includes two blister sheet displacement mechanisms and requires the blister sheet having the medicament to be punctured at the site of dispensing to release the medicament, rather than the lid sheet being peeled away; so, the function of the receiver element is merely to take up the loose used elongate carrier.

Therefore, in light of the foregoing discussion, there exist opportunities to provide simpler mechanisms than are found in medicament dispensers of the prior art, and to provide an efficient, reliable, cost-effective and easy-to-use medicament dispenser.

SUMMARY

The present disclosure seeks to provide a medicament dispenser for holding at least one elongate form medicament carrier. The present disclosure also seeks to provide a method of assembling the medicament dispenser. The present disclosure seeks to provide a solution to the existing problem of complex conventional medicament dispensers and potential failure associated therewith during progression of the medicament carrier in the medicament dispenser. An aim of the present disclosure is to provide a solution that overcomes at least partially the problems encountered in prior art, and provides a reliable, effective, robust mechanism for dispensing medicament doses while maintaining the integrity of the medicament carrier during progression thereof in the medicament dispenser.

The present disclosure is particularly applicable for inhalation delivery, or an inhalation delivery device, in particular a dry powder inhaler.

In one aspect, an embodiment of the present disclosure provides a medicament dispenser for holding at least one elongate form medicament carrier, the at least one elongate form medicament carrier having a proximal end, a distal end, and a blister elongate sheet and a lid elongate sheet enclosing multiple distinct medicament dose portions therebetween,

- the medicament dispenser having a dispensing mechanism which is adapted to operate, upon each actuation of the medicament dispenser, to dispense a medicament active from a medicament dose portion of the at least one elongate form medicament carrier, said mechanism comprising:
  - at least one power spring mechanism for winding the lid elongate sheet, wherein the at least one power spring mechanism comprises:
    - at least one spring having an inner end about which the at least one spring unwinds, and
    - at least one shaft at which the inner end of the at least one spring is secured,
- wherein the power spring mechanism tensions and peels a segment of the lid elongate sheet peeled from a corresponding segment of the blister elongate sheet upon each actuation of the medicament dispenser.

In another aspect, an embodiment of the present disclosure provides a method of assembling the medicament dispenser according to any of the preceding claims, the method comprising:

- inserting at least one elongate form medicament carrier into at least one receiving portion of the medicament dispenser, the at least one elongate form medicament carrier having a proximal end, a distal end, and a blister elongate sheet and a lid elongate sheet enclosing multiple distinct medicament dose portions therebetween;
- anchoring a distal end of the blister elongate sheet to a take-up spool of the medicament dispenser;
- assembling the at least one power spring mechanism of the medicament dispenser, such that an inner end of the at least one spring is secured to at least one shaft;
- anchoring a distal end of the lid elongate sheet by or near to an outer end of the spring;
- receiving at least one medicament dose portions of the at least one elongate form medicament carrier on the at least one receiving capstan; and
- tensioning the lid elongate sheet and the blister elongate sheet on the at least one power spring mechanism and the take-up spool respectively.

Embodiments of the present disclosure provide improvements over the prior art, and enable delivery of multiple distinct medicament doses in a single combined dosage whilst reducing rucking or over tensioning of the elongate form medicament carrier and misfeeding the elongate form medicament carrier around the receiving capstan. They also improve spooling the lid elongate sheet by the power spring mechanism, optionally, around the bobbin, thereby better controlling the tension in the medicament carrier. Moreover, the disclosed medicament dispenser employs a common mechanism, i.e. peeling off the lid elongate sheet from the blister elongate sheet, to dispense the medicament as well as effectively spooling the peeled lid elongate sheet by the power spring mechanism, optionally, on the bobbin, and the peeled blister elongate sheet on the take-up spool. Furthermore, control of the tension in the lid elongate sheet by the power spring mechanism is independent of any gear mechanism to drive the receiving capstan, such that spooling of the lid elongate sheet cannot get out of step with spooling of the blister elongate sheet.

Additional aspects, advantages, features and objects of the present disclosure will be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those skilled in the art will understand that the drawings are not to scale. Wherever possible, like elements have been indicated by identical numbers.

Embodiments of the present disclosure will now be described, by way of example only, with reference to the following diagrams wherein.

Figure 1A:
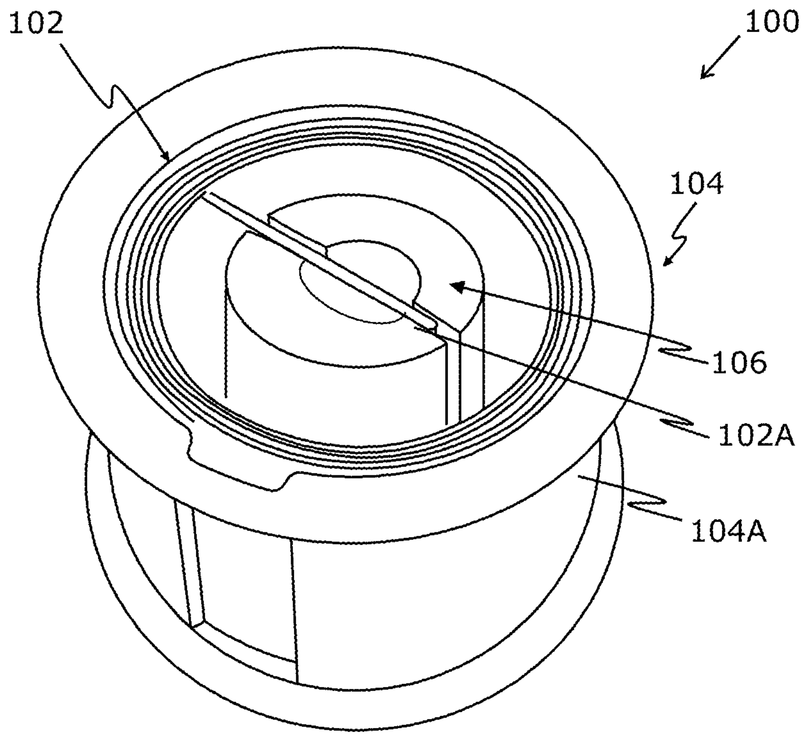
FIGS. 1A, 1B, 1C and 1D are schematic views of a power spring mechanism, in accordance with an embodiment of the present disclosure.

In the accompanying drawings, a non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art will recognize that other embodiments for carrying out or practising the present disclosure are also possible.

The present disclosure provides the aforementioned medicament dispenser and the aforementioned method of assembling the medicament dispenser. The disclosed system and method ensure accurate lid sheet peeling from a blister sheet, by a predictable mechanical means. In this regard, the medicament dispenser comprises an undriven spring that moves naturally from a stressed state to a relatively unstressed state to maintain tension within a suitable range on the lid elongate sheet. Additionally, the spring enables the medicament dispenser to perform both functions of peeling the lid elongate sheet from the blister elongate sheet to expose (namely, dispense) medicament as well as spooling the lid elongate sheet by the power spring mechanism, optionally, over the bobbin, for a compact waste storage.

The medicament dispenser is a robust, user-friendly, and simple to manufacture and assemble system with an optimal performance thereof. The medicament dispenser effectively spools the lid elongate sheet and eliminates slack thereof throughout the usage of the medicament dispenser.

In an embodiment, beneficially, the medicament dispenser effectively exposes the medicament upon each actuation of the medicament dispenser, thereby, preventing the blister elongate sheet from exposing the medicament in advance and leaving it liable to become contaminated and/or degraded by atmospheric conditions thereafter. The receiving capstan is configured to hold medicament dose portions in fixed positions until actuation of the medicament dispenser.

In another embodiment, the medicament dispenser is designed to hold more than one, such as two or more, elongate form medicament carriers with relatively greater ease, thereby simplifying the assembly of the medicament dispenser and reducing the mechanisms required to drive the dispensing mechanism during use. Furthermore, such design of the medicament dispenser enables the dispensing of multiple bioactive components that may be taken in by the user in combination or sequentially. Accordingly, the medicament dispenser may comprise two power spring mechanisms, one for each elongate form medicament carrier.

Pursuant to embodiments of the present disclosure, there is provided a medicament dispenser for holding at least one elongate form medicament carrier. The term "elongate form medicament carrier" as used herein refers to a strip (or portion of a strip), fabricated from a thin sheet of flexible material or sheets of flexible materials, bearing medicament (namely, medicament formulation or medicament product). Such medicament carriers may be used to administer a prescribed medicament (namely, medicament active or medicament actives) to an intended user, for example a patient suffering from a respiratory illness and associated symptoms. It will be appreciated that a plurality of such elongate form medicament carriers could be employed to administer a plurality of medicament actives, in combination or sequentially, useful for a variety of conditions such as asthma, pulmonary diseases such as COPD (chronic obstructive pulmonary disease), and so forth. The plurality, e.g., two, elongate form medicament carriers may be manufactured as a single strip.

The at least one elongate form medicament carrier has a proximal end, a distal end, and a blister elongate sheet and a lid elongate sheet enclosing multiple distinct medicament dose portions therebetween. The proximal end and the distal end are opposite to each other. It may be appreciated that the proximal end may refer to an end near to the bulk of the unused elongate form medicament carrier and the distal end may refer to an end that is farther away from the bulk of the unused elongate form medicament carrier. Moreover, the elongate form medicament carrier comprises a pair of elongate sheets (namely, the blister elongate sheet and the lid elongate sheet), that have been attached together, between the proximal end and the distal end. Furthermore, the blister elongate sheet has multiple distinct medicament dose portions for storing a medicament active, while the lid elongate sheet, corresponding to the size of the blister elongate sheet, covers or seals the multiple distinct medicament dose portions (carrying medicament actives therein) on the blister elongate sheet. The term "medicament dose portion" as used herein refers to a measured quantity contained within a blister of the blister elongate sheet. The administrable dose is a whole number multiple of the medicament dose portion. Usually, one administrable dose can be provided in one medicament dose portion. However, it may be desirable to provide the administrable dose in two or more medicament dose portions. The administrable dose of the single medicament may be provided in at least one blister and combined with an administrable dose of another single medicament to provide a final dose for the patient. Alternatively, at least one of the administrable doses may comprise two or more medicaments.

Notably, the proximal end of the elongate form medicament carrier is employed to carry the multiple distinct medicament dose portions for carrying the medicament active. Optionally, the multiple distinct dose portions are uniformly spaced on the elongate form medicament carrier starting from the proximal end thereof. Optionally, the spacing of the multiple distinct medicament dose portions in two or more elongate form medicament carriers may be similar or different from each other. Notably, the distal end of the elongate form medicament carrier does not comprise multiple distinct medicament dose portions for carrying the medicament active and appears as a flat foil, optionally, with a looped end thereof.

Optionally, the elongate form medicament carrier may be manufactured from a plastic material, an aluminium foil, a combination thereof, or any other suitable material, and may comprise recesses for forming pockets or blisters. Optionally, the blister elongate sheet and the lid elongate sheet could be manufactured from a same or different fabrication material.

Optionally, the lid elongate sheet is fabricated from at least one of: a paper, a polyester, an aluminium foil. Optionally, the blister elongate sheet is fabricated from at least one of: an oriented polyamide (OPA), an aluminium foil, a polymeric material. Optionally, both the lid elongate sheet and the blister elongate sheet are fabricated as a multi-layered construction using a combination of metal, paper and polymeric materials. Beneficially, such multi-layered construction ensures a strong and reliable implementation of the lid elongate sheet and blister elongate sheet, thereby providing a superior barrier layer between the external contaminants and the medicament actives. Moreover, the lid elongate sheet is coated with a heat seal lacquer for bonding to the blister elongate sheet. Beneficially, the heat seal lacquer provides a sturdy hermetic sealing between the lid elongate sheet and the blister elongate sheet, except in the blisters (or central regions) of the medicament dose portions and the inner ends of the lid elongate sheet or the blister elongate sheet, as applicable, ideally in such a manner that the lid elongate sheet and the blister elongate sheet can be peeled apart. Optionally, the lid elongate sheet and the blister elongate sheet may be bonded using bonding, welding, or any other method known to a person skilled in the art.

In a variation of the blister strips, two elongate form medicament carriers, operable to dispense two different doses in combination or sequentially to the user, could be combined in a blister strip. Accordingly, the blister strip may comprise a first medicament dose portion and a second medicament dose portion corresponding to the first and second elongate carriers, respectively. The distal end of the first portion has a first end region and the distal end of the second portion has a second end region and there is a length of foil between the two portions. The first end region is proximal to the first medicament dose portion of the first portion. The second end region is proximal to the second medicament dose portion of the second portion. The aforementioned length of foil between the two portions of the blister strip comprises no medicament dose portions. Optionally, the length of foil is at least partially formed into a closed loop. In such arrangement, the length of foil of both the elongate form medicament carriers may be combined together face-to-face to form a unified length and the second end regions of the two elongate form medicament carriers could be combined (or connected) to form a common closed loop. It will be appreciated that the unified length comprises only the length of foil of the blister elongate sheets, while the corresponding segments of the lid elongate sheets are peeled and harnessed to the dispensing mechanism, such as corresponding bobbins. Moreover, the two elongate form medicament carriers are forked from the unified length at the distal end regions thereof. In such arrangement, the common loop brings the two elongate form medicament carriers into a folded-configuration such that the lid elongate sheet corresponding to one elongate form medicament carrier faces the lid elongate sheet corresponding to the other elongate form medicament carrier. Optionally, the unified length is preferably permanently connected, such as by bonding, welding, and the like, to create such a bond. Beneficially, the unified length enables progression or advancement of the two elongate form medicament carriers manufactured as a single strip. at the same rate, when in operation.

Optionally, the unified length is 5 millimetres to 30 millimetres long. The unified length may be for example from 5, 10, 15, 20 or 25 millimetres (mm) up to 10, 15, 20, 25 or 30 mm long. The term "loop" as used herein refers to a "hair-pin like" structure achievable by folding of the second end region of the distal end of the at least one elongate form medicament carrier. It will be appreciated that the lid elongate sheet may be similar in size to or slightly longer than the blister elongate sheet. Moreover, optionally, the distal end of the lid elongate sheet provides a structure similar to a lift-tab for peeling the lid elongate sheet from the blister elongate sheet to expose the medicament dose portions. Moreover, the lift-tabs provided may be harnessed to a dispensing mechanism, such as a bobbin, to wind on the lid elongate sheet. Furthermore, the distal end of the blister elongate sheet, after peeling the lid elongate sheet therefrom, may be harnessed to a dispensing mechanism, such as a take-up spool.

The term "medicament active" as used herein refers to a pharmaceutical compound/drug, a vaccine or genetic material combined with a vector, administered to a user for healing, treating, altering, improving, restoring, relieving, and/or curing a particular condition, disease, or mental or physical state. Notably, the medicament active includes an active ingredient or a combination of active ingredients and inactive ingredients, optionally mixed with an excipient or dissolved in some other carrier for delivery to the user. Furthermore, the mixture of medicament actives comprises a plurality of pharmaceutical compounds, wherein the plurality of pharmaceutical compounds does not react with each other.

Optionally, the medicament active is at least one active pharmaceutical ingredient (API) having a physiological effect when ingested or otherwise introduced into the body of the user (namely, a patient). In an example, the drug is an anti-inflammatory drug (such as a corticosteroid, or any other steroid), or a bronchodilator (such as a Long-acting beta agonist (LABA) or a long-acting muscarinic receptor agonist (LAMA)) for a patient suffering from asthma or chronic obstructive pulmonary disease (COPD). Notably, the bronchodilator as the medicament active is employed for dilating bronchi and bronchioles of the patient it is administered to and for increasing airflow to the lungs. Furthermore, when an anti-inflammatory drug is used as the medicament active component, it is employed to reduce swelling in the patient, decrease airway sensitivity caused by inflammation and reduce mucus production. Optionally, the at least one API may be combined with at least one excipient. The excipient is an inactive substance that aids in the manufacturing process and/or to protect, support, enhance stability, bioavailability or patient acceptability of an active substance, such as drug or other active substances. Optionally, the excipients serve as a carrier or medium for a drug or other active medicament to reach its target site in the body of the patient. Optionally, excipients may include, but are not limited to, fillers, preservatives, colouring agents, antioxidants, binders, anticoagulating agents, coating agents, emollients, emulsifying agents.

Moreover, the powdered form of the medicament active is available to the user of the medicament dispenser when the medicament dispenser is in use thereby.

Optionally, each medicament dose portion of the elongate form medicament carrier comprises a single active medicament component. Alternatively, each medicament dose portion of the elongate form medicament carrier comprises a plurality (i.e., more than one) of active medicament components, such as in a plurality of sets of medicament dose portions. Optionally, the dose portions in the two or more elongate form medicament carriers may be similar or different in terms of: a type (namely a drug type, such as a bronchodilator or an anti-inflammatory drug) of medicament active, a form (namely, a powdered form, a tablet or a liquid) of medicament active, an amount (namely, a higher amount or a lower amount) of medicament active, a frequency of administering of medicament active, and so forth. It will be appreciated that the dose portions in the two or more elongate form medicament carriers may be chosen with regard to at least one of: patient's age, symptoms, severity of condition, a prescribed medication, and medication side effects.

Moreover, those skilled in the art will recognize that other embodiments for carrying out or practising the present disclosure are also possible. For example, it may be understood by a person skilled in the art that the use of two elongate form medicament carriers is merely an example for sake of clarity, which should not unduly limit the scope of the claims herein. The person skilled in the art will recognize many variations, alternatives, and modifications of embodiments of the present disclosure, such as use of a single-strip elongate form medicament carrier by bonding, in hair-pin like loop turn, an end of the said single-strip elongate form medicament carrier not containing the medicament dose portions (namely, the length of foil) upon itself to result in an additional region for reliably enabling the used single-strip elongate form medicament carrier to be collected.

Moreover, the at least one elongate form medicament carrier is inserted in the medicament dispenser. The term "medicament dispenser" as used herein refers to a portable medicine storage unit for users for dispensing any number of medications to the users when required. In an embodiment, the medicament dispenser may be implemented as a dry powder inhaler (DPI). The medicament dispenser has a dispensing mechanism which is adapted to operate, upon each actuation of the medicament dispenser, to dispense a medicament active from a medicament dose portion of the at least one elongate form medicament carrier. It will be appreciated that at a time, upon each actuation of the medicament dispenser, at least one medicament active is dispensed from at least one medicament dose portion of the at least one elongate form medicament carrier. For example, at a time, two medicament dose portions corresponding to each of the two elongate form medicament carriers, manufactured as a single strip, may dispense medicament actives therein, upon each actuation of the medicament dispenser. Moreover, the dispensing mechanism is operable to dispense said medicament active(s) upon actuation of the medicament dispenser by the user. It will be appreciated that the medicament dispenser is provided with an actuation means thereon, wherein the user uses the actuation means to cause actuation of the medicament dispenser to dispense or release the medicament active from the medicament dose portion of the at least one elongate form medicament carrier. In an embodiment, the actuation means is implemented as a mouthpiece cover or a nosepiece cover of the dispenser, wherein the user uncovers and sucks or inhales via the mouthpiece cover or the nosepiece cover respectively, to trigger the release of the medicament dose. In another embodiment, the actuation means is implemented as a slider, or a button, wherein the user slides the slider or presses the button to trigger the release.

Moreover, the dispensing mechanism comprises:

- at least one power spring mechanism for winding the lid elongate sheet, wherein the at least one power spring mechanism comprises:
  - at least one spring having an inner end about which the at least one spring unwinds, and
  - at least one shaft at which the inner end of the at least one spring is secured,
- wherein the power spring mechanism tensions and peels a segment of the lid elongate sheet peeled from a corresponding segment of the blister elongate sheet upon each actuation of the medicament dispenser.

In this regard, the power spring mechanism may comprise a tightly wound spring made from a flat strip of spring material that is cut to length and wound around a forming arbour (namely, the shaft) and unwound into a housing (such as a housing defined by side wall of a bobbin). Specifically, the inner end of the spring may be bent and attached to the shaft (located inside the housing), such that each turn rests on its inner neighbour, and an opposite, free outer end may be attached to the housing, i.e. the side wall of the bobbin. Moreover, the power spring mechanism is designed to store mechanical energy and works by creating rotational energy in either the shaft or the bobbin, producing usable torque. In the disclosed mechanism, the rotational energy is imparted to the bobbin, while the shaft is immobile. Notably, the torque generated increases as the spring is wound tighter and decreases as it unwinds.

The spring may be a coiled spiral spring, based on a ribbon of a springy material. It will be appreciated that the shaft has a compact structure that occupies a small space inside the housing, and a proportion of the rest of the space inside the housing is occupied by the coiled spiral spring. It will be appreciated that the diameter of the shaft with respect to the diameter of the housing affects the available space inside the housing and therefore the number of available turns in the coiled spiral spring (for example 10-35 turns). Additionally, the number of available turns and the material properties and the dimensions (length, width and thickness) of the coiled spiral spring define the performance thereof. Beneficially, the coiled spring may be configured such that the torque exerted by the power spring mechanism, corresponding to the last medicament dose portion dispensed by the device, is above a threshold torque value. Further, the threshold torque value is preferably sufficient to peel the lid elongate sheet from the blister elongate sheet. Furthermore, the threshold torque value is preferably less than the torque value that would cause the first medicament dose portion dispensed from the device to be prematurely opened.

The outer end of the spring is configured to anchor thereon the distal end of the lid elongate sheet of the at least one elongate form medicament carrier. Moreover, the spring may be configured to wind the lid elongate sheet thereon, starting with the distal end of the lid elongate sheet and continuing to consistently wind subsequent portions of the lid elongate sheet (that have been peeled apart from the corresponding blister elongate sheet) after dispensing doses from the medicament dose portions.

Optionally, the dispensing mechanism further comprises a bobbin which is hollow and cylindrical, an outer end of the at least one spring being secured at a side wall of the bobbin, the at least one shaft being at least partially positioned within the bobbin. Herein, the bobbin is implemented as a hollow and cylindrical case that may be made of a metal or plastic. The hollow and cylindrical bobbin has a cavity wherein the at least one spring may be held by the outer end such that it imparts a torque to the bobbin and rotates the bobbin, while the shaft remains immovable inside the bobbin. Notably, the outer end of the at least one spring is anchored to the at least one bobbin at an inner side wall thereof. Moreover, the at least one shaft is positioned within the hollow and cylindrical bobbin to retain the inner end of the spring therein, about which the spring unwinds. As mentioned above, it will be appreciated that the shaft occupies a small space inside the bobbin, and a proportion of the rest of the space inside the bobbin is occupied by the coiled spiral spring.

In such case, the bobbin may anchor the distal end of the lid elongate sheet of the at least one elongate form medicament carrier thereon at or near an outer side wall of the bobbin. Moreover, the at least one bobbin may be configured to wind the lid elongate sheet thereon, starting with the distal end of the lid elongate sheet on the at least one bobbin, and continuing to wind subsequent portions of the lid elongate sheet (that have been peeled apart from the corresponding blister elongate sheet) onto the at least one bobbin after dispensing doses from the medicament dose portions. Optionally, the bobbin surface onto which the lid elongate sheet is wound is barrel-shaped. Preferably, the barrel shape provides a larger diameter centrally than at the edges, corresponding to the centre and edges widthways across the lid elongate sheet. For example, the central diameter may be in the range from 0.1 to 2 mm greater than the edge diameters, e.g., 0.25 to 2 mm, which are preferably equal to each other. The barrel shape improves reliability of consistent winding, avoiding lateral displacement of the lid elongate sheet as it is wound. Herein, the at least one bobbin is capable of a rotational motion to aid winding of the lid elongate sheet thereon.

Optionally, the bobbin has a rotational axis and the at least one spring is arranged to unwind about the rotational axis of the bobbin, wherein the rotational axis of the bobbin is the axis about which the bobbin rotates. As mentioned before, the shaft is positioned at least partially within the bobbin and oriented parallel to the rotational axis of the bobbin, while the at least one shaft is optionally immobile such that the at least one spring imparts rotational energy to the bobbin. Preferably, the spring unwinds about the rotational axis of the bobbin. Moreover, unwinding of the spring in a unidirectional manner results in a unidirectional rotation of the bobbin. Preferably, the shaft is positioned substantially to encompass the rotational axis of the bobbin.

Optionally, the shaft is coaxial with the bobbin. Moreover, coaxial arrangement of the shaft inside the bobbin eliminates a potential wobbling of the bobbin and makes the medicament dispenser steady during operation. Furthermore, coaxial arrangement of the shaft inside the bobbin results in a higher number of available turns in the power spring.

Optionally, the shaft is mounted in the medicament dispenser in a manner to prevent movement of the shaft when the medicament dispenser is in use. In this regard, optionally, a unidirectional spring winding rotation of the at least one shaft relative to the at least one bobbin, used during initial assembly of the power spring mechanism into the medicament dispenser, is then retained by at least one of: a ratchet, a clip, a clutch or a stopper. Specifically, the ratchet, the clip, the clutch or the stopper, and the like when arranged in the medicament dispenser prevent the at least one shaft from rotating as the at least one spring subsequently winds or unwinds during the use of the medicament dispenser upon actuation thereof. Moreover, the power spring mechanism may comprise the ratchet, the clip, the clutch or the stopper, and the like, arranged such that the at least one shaft may be locked into place relative to the at least one bobbin during assembly of the power spring mechanism, so that the at least one spring is not driven in either direction during use of the medicament dispenser device.

In this regard, the term "ratchet" as used herein refers to a mechanical device that allows continuous linear or rotary motion in one direction while preventing motion in the opposite direction. Moreover, the ratchet is used as a means of holding the at least one shaft in a tensioned state. Alternatively, the at least one spring and the at least one elongate form medicament carrier may be inserted in a pretensioned state for smooth running of the medicament dispenser. Notably, a ratchet comprises a pawl. The pawl consists of a pivoting bar whose free end engages with the teeth of a cogwheel or gear, so that the cogwheel or gear can only turn or move in one way (namely, direction). It typically engages the gear at a steep angle so that it can be made to ride over the teeth when the cogwheel is turned in the correct direction of rotation, but digs into the teeth when the cogwheel is turned in the incorrect direction of rotation. The term "clip" as used herein refers to a device that grips, clasps, or hooks an object. The clip is a metal or plastic clip working with the at least one shaft. Specifically, the at least one shaft is pushed into the clip for secured retention thereof, and pulled out to be released. The term "clutch" as used herein refers to a coupling or a locking mechanism used to connect and disconnect a driving and a driven part of a mechanism, such as the dispensing mechanism. The clutch may be a dog clutch (also known as dog gears). The dog clutch is a type of clutch that couples at least shafts or other rotatable components not by friction but by interference or clearance fit. Moreover, the two parts of the clutch are designed such that one will push the other, causing both to rotate at the same speed without slipping. The term "stopper" as used herein refers to a component that brings to a halt or stop an operating or functioning element of the device. The stopper may be used to control or stop the rotation of the at least one shaft, upon each actuation of the medicament dispenser, to dispense a medicament active from the medicament dose.

Optionally, the at least one spring peels a segment of the lid elongate sheet from a corresponding segment of the blister elongate sheet. The term "unwinding" as used herein refer to uncoiling or rotation of the at least one spring to wind about the inner end thereof inside the hollow cylindrical bobbin, thereby peeling the lid elongate sheet with each dose indexing. It will be appreciated that unwinding of the at least one spring provides rotational energy, via the outer end of the at least one spring, to the bobbin, at an inner side of the side wall of which the at least one spring may be attached. Moreover, at the outer side of the side wall of the bobbin the distal end of the lid elongate sheet, separated from the distal end of the blister elongate sheet, may be attached. Such attachment may be to the outer side wall of the bobbin or to the outer end of the at least one spring. The rotation of the at least one bobbin, in response to the unwinding of the at least one spring, tensions the lid elongate sheet thereby, thus peeling a segment of the lid elongate sheet from a corresponding segment of the blister elongate sheet of the at least one elongate form medicament carrier and further separates the lid elongate sheet and the blister elongate sheet, upon each actuation of the medicament dispenser. Moreover, for each pre-defined unwinding a corresponding medicament dose portion, sealed by said segment of the lid elongate sheet, is exposed for dispensing the medicament active therein. Notably, the at least one spring undergoes the pre-defined unwinding until a last medicament dose portion is exposed to dispense a last medicament active stored therein.

Optionally, the outer end of the at least one spring anchors the distal end of the lid elongate sheet thereto. In this regard, the distal end of the lid elongate sheet is directly anchored to the outer end of the at least one spring attached to the side wall of the bobbin, rather than the bobbin. Therefore, as the spring winds or unwinds, a segment lid elongate sheet is pulled from the corresponding segment of the blister elongate sheet, and is tensioned by the bobbin.

Optionally, the at least one spring is ribbon-shaped or coiled-ribbon-shaped, such as to take the form of a spiral spring when assembled in the power spring mechanism. The at least one spring winds into a concentrically aligned coil during the assembly of the device and is held by a maximum traction force. The traction force refers to force used to generate motion between a body and a tangential surface by dry friction. During the dispensing of the dose, the at least one spring loses some of its tension due to the reduction of the traction force and unwinds causing the bobbin to rotate and tension the lid elongate sheet thereon. Notably, the power spring mechanism may have any spring, but not limited to, clock spring, coil spring, mainspring, hair spring, wind spring, spiral spring, recoil spring, retractor spring, constant force spring.

Optionally, the at least one spring is fabricated from any one or more of: a metal, an alloy of metal, a plastic, a paper or a rubber. The spring may be fabricated from a metal e.g., copper, iron, beryllium, titanium, and the like. The metal alloys include for example stainless steel, carbon steel, chrome silicon (chromium and silicon alloy), chrome vanadium (chromium and vanadium alloy), elgiloy (cobalt, chromium and nickel alloy) phosphor bronze, brass, and the like. It will be appreciated that the spring could be fabricated from paper, rubber and plastic, for example plastic composites, polyphenylene sulfide, acrylonitrile butadiene styrene (ABS), nylon, acrylic, polyamide-imide (PAI) and the like. Notably, the spring fabrication material desirably has a high strength and a high elastic limit. The springs are designed to undergo large deflections over their usage; the fabrication material must also have an extensive elastic range to perform efficiently throughout use. In an example, the power spring mechanism includes a spring produced from a strip of a flat tempered steel that is wound tightly into a spiral configuration. Typically, the strength of the spring fabrication material, such as for example steel, may be 400 Megapascal (MPa), and the elastic limit of the aforesaid steel-based spring fabrication material, may be $21\times10^4$ MPa.

Optionally, the dispensing mechanism further comprises:

at least one receiving portion for receiving the at least one elongate form medicament carrier having multiple distinct medicament dose portions, the receiving portion comprising:

at least one receiving capstan for receiving the medicament dose portions of the at least one elongate form medicament carrier; and

- a manifold, associated with at least one receiving capstan, for dispensing the medicament active from each of the medicament dose portions of the at least one elongate form medicament carrier; and
- a take-up spool for holding a distal end of the blister elongate sheet.

In this regard, the at least one receiving portion generally refers to at least one chamber of the medicament dispenser in which the at least one elongate form medicament carrier is inserted. Specifically, the receiving portion comprises the at least one receiving capstan to receive the medicament dose portions of the at least one elongate form medicament carrier. Optionally, the receiving portion may be implemented as a single receiving portion that receives at least one elongate form medicament carrier, such as two or more elongate form medicament carriers.

Alternatively, optionally, the receiving portion may be implemented as plural distinct receiving portions for receiving respective elongate form medicament carriers. In such case, each of the plural distinct receiving portions comprises a receiving capstan to receive a respective elongate form medicament carrier. In an example, a first receiving capstan in a first receiving portion receives a first elongate form medicament carrier, a second receiving capstan in a second receiving portion receives a second elongate form medicament carrier, and so forth.

Moreover, the at least one receiving capstan is in the form of a dimpled cylinder. More specifically, dimples of the at least one receiving capstan may appear as recesses that register (or position) the medicament dose portions adjacent to the manifold. In this regard, the at least one receiving capstan comprises a plurality of recesses for accommodating multiple distinct medicament dose portions (such that one medicament dose portion is registered in one recess) of the at least one elongate form medicament carrier and a given capstan positions a given medicament dose portion adjacent to the manifold for delivery (such as in a 'First In First Out' (FIFO) sequence) thereof. Moreover, upon rotation of the at least one receiving capstan in order to advance a medicament dose portion thereon adjacent to the manifold, the medicament active in the medicament dose portion is dispensed and presented to the manifold.

The manifold is positioned to be in communication in turn with the distinct medicament dose portions releasable by the dispensing mechanism to enable dispensing the medicament active therein to the user. Optionally, the manifold has an opening for inhalation of the dispensed medicament active by the user. Optionally, the manifold may comprise an opening corresponding to the at least one elongate form medicament carrier. In this regard, the term "opening" as used herein refers to a hole or an empty space in the manifold of the medicament dispenser. Typically, the openings are provided adjacent to the at least one receiving capstan that positions at least one medicament dose portion adjacent to the manifold for delivery thereof. Optionally, a single common manifold passage is provided, which communicates in turn with the distinct medicament dose portions of the at least one elongate form medicament carrier via the respective opening of the manifold. Notably, a single distinct medicament active from the medicament dose portion, adjacent to the manifold, is received into the single common manifold passage for inhalation by the user. Optionally, said common manifold passage is shaped to encourage mixing of said released medicament dose portions. Herein, the term "inhalation" refers to an act of inhaling or drawing air into the lungs for breathing or respiration process of the user. Advantageously, the elongate form medicament carrier is practically airtight around the opening thereof, in order to control airflow to the medicament dose portion to dispense it. In an example, the user may apply suction to the exposed medicament dose portions (once the lid elongate sheet and the blister elongate sheet are separated as a result of the peeling action by the dispensing mechanism) through the opening in the manifold. Optionally, the manifold provides an access (implemented as a mouthpiece or nosepiece of the medicament dispenser) between a compartment of the medicament dispenser housing the elongate form medicament carrier and a chamber for mixing a dispensed dose with an airstream for delivery to a patient. Specifically, when the user applies a suction to a mouthpiece or a nosepiece of the medicament dispenser, due to the change in pressure an airstream (namely, an airflow) is introduced into the medicament dispenser. Such airstream may carry the medicament active from the medicament dose portions via the manifold to the user. Alternatively, optionally, there are two manifolds, one for each of the two elongate form medicament carriers.

The take-up spool winds up the distal end of the blister elongate sheet of the at least one elongate form medicament carrier. It will be appreciated that while inserting the at least one elongate form medicament carrier in the medicament dispenser, the lid elongate sheet and the blister elongate sheet of the at least one elongate form medicament carrier are partially separated at the distal ends thereof and that each of the distal ends is harnessed on a respective bobbin and take-up spool. Specifically, the distal end of the blister elongate sheet is affixed to the take-up spool to spool the used blister elongate sheet thereon, starting with the distal end of the blister elongate sheet and continuing to wind the used portions (i.e. after dispensing doses from the medicament portions) of the blister elongate sheet, upon rotation of the take-up spool. The mechanism of the take-up spool is triggered by the actuation means triggering the release of the medicament active from the respective medicament dose portions. Specifically, the actuation means may trigger the rotation of the take-up spool such that the used blister elongate sheet is wound up around the take-up spool. Optionally, the rotation motion of the take-up spool enables the peeling apart of the lid elongate sheet from the blister elongate sheet. Specifically, a spooling mechanism of the take-up spool results in the used blister elongate sheet coiling in on itself as further portions of the blister elongate sheet are fed through the receiving capstans towards the take-up spool. Optionally, the radius of the take-up spool is less than the radius of the at least one capstan. Notably, a small radius of the take-up spool reduces the length of the elongate form medicament carrier wound thereon as well as the slack condition in the elongate form medicament carrier, thus overcoming a jamming condition.

Optionally, the take-up spool comprises a peg for securing the distal end of the blister elongate sheet. Specifically, the peg is implemented as a short pin or bolt, around which the distal end of the blister elongate sheet is secured. Moreover, the distal end of the blister elongate sheet has a loop which is attached to the peg to spool the used blister elongate sheet. Optionally, the peg is positioned away from the axis of rotation of the take-up spool and rotates by exerting a pressure on the loop of the blister elongate sheet to enable winding of the blister elongate sheet on the take-up spool. The peg is typically positioned parallel to an axis of rotation of the take-up spool. The axis of rotation is the centreline of the take-up spool about which the take-up spool rotates. The rotation of the take-up spool results in a rotational motion of the attached loop of the distal end of the blister elongate form sheet. Notably, the direction of winding of the blister elongate sheet on the take-up spool is opposite to the direction of unwinding of the elongate form medicament carrier from the at least one receiving capstan.

Optionally, the dispensing mechanism is configured to drive the at least one receiving capstan and the take-up spool with gears. The term "gears" as used herein refers to an arrangement, e.g., of intermeshed cog wheels, that is configured to ensure that the medicament dose portion has been exposed upon exit of a specific length of elongate form medicament carrier from the at least one receiving portion. As the arrangement of gears changes a relative position thereof, the corresponding components of the medicament dispenser rotate including the take-up spool, thereby, winding the blister elongate sheet on the take-up spool.

In an exemplary implementation, the gearing arrangement comprises a plurality of gears driven through a cover driver gear. The term "cover driver gear" as used herein refers to a gear that is driven by the opening and or closing of the mouthpiece cover or the nosepiece cover. The cover driver gear is coupled with a plurality of receiving capstan gears, or a single capstan gear. The plurality of receiving capstan gears may comprise a first receiving capstan gear coupled to a second receiving capstan gear, wherein the first receiving capstan gear drives the first receiving capstan and the second receiving capstan gear drives the second receiving capstan. Alternatively, the single capstan gear may drive two or more receiving capstans, such as the first receiving capstan and the second receiving capstan. Furthermore, the cover driver gear is coupled to a take-up spool gear wherein, the take-up spool gear drives the take-up spool using a connecting gear.

Optionally, the power spring mechanism peels the segment of the lid elongate sheet corresponding to the at least one receiving capstan receiving a medicament dose portion. It will be appreciated that the gear arrangement of the medicament dispenser enables the at least one bobbin, the at least one receiving capstan and the take-up spool to rotate. Notably, rotation of the at least one bobbin, achieved by the power spring mechanism, results in the at least one spring undergoing the pre-defined unwinding, thereby peeling a segment of the lid elongate sheet corresponding to the segment of the elongate medicament sheet between a pair of adjacent medicament dose portions. It will be appreciated that the medicament dose portions are held sequentially in the recesses of the at least one receiving capstan, and the friction of engagement between the receiving capstan and the gear arrangement prevents the at least one spring from rapidly unwinding and peeling the lid elongate sheet too far from the blister elongate sheet. Therefore, high tension in the at least one spring is made possible, and the lid elongate sheet is only peeled by an amount presented by indexing of the medicament dose portions, even when such high tension is applied. Moreover, it will be appreciated that the size or diameter of the at least one bobbin remains the same size throughout the usage of the medicament dispenser while the outer diameter of the spooled lid elongate sheet increases as the used lid elongate sheet is collected. Therefore, the at least one bobbin is required to have a reducing angular rotation to ensure consistent lid elongate sheet advancement lengths as the spooled lid elongate sheet diameter grows for sequential indexing of the medicament dose portions throughout the usage of the medicament dispenser. The disclosed mechanism provides for such reducing angular rotation automatically.

Optionally, the medicament dispenser has walls that surround the elongate form medicament carrier and also provide a peel point for directing the lid elongate sheet away from the trajectory provided for the blister sheet around the receiving capstan, such as the first or the second receiving capstan. The relative positions of the peel point and the receiving capstan, the tension provided by the power spring mechanism and the adhesion of the lid elongate sheet to the blister elongate sheet result in the angle at which the lid elongate sheet is peeled from the blister elongate sheet. Such an angle may be measured between the tensioned lid elongate sheet, between the peel point and the receiving capstan, and a tangent to the blister sheet, nearest to where the lid elongate sheet is peeled, at the receiving capstan. Preferably, said angle is in a range from 70° to 110°. The said angle may for example be from 70, 80, 90 or 100° up to 80, 90, 100 or 110°.

Moreover, the tension in the lid elongate sheet can be adjusted to ensure that the blister elongate sheet is pulled into the dimples of the at least one receiving capstan closer to be presented to the manifold to dispense the medicament actives from the blisters, thereby impacting the location of the blister, and that there is a relatively airtight engagement between the blister elongate sheet and the manifold. Optionally, besides the tension in the lid elongate sheet, the geometry around the peel point and the at least one receiving capstan also contributes to the airtight engagement between the blister elongate sheet and the manifold. Therefore, various components of the medicament dispenser, such as the tension in the lid elongate sheet, the manifold, the at least one receiving capstan and the peel point, impact the exact location of the blisters with respect to the manifold. It will be appreciated that the torque/force required to drive the lid elongate sheet to be peeled and held taut by the power spring mechanism is mostly provided by the tension in the lid elongate sheet (and the take-up spool that holds taut the corresponding part of the used blister elongate sheet), with the role of the at least one capstan being largely to position the blisters for presenting the medicament active therein.

Optionally, the at least one shaft is arranged on an axis parallel to the axis of rotation of the at least one receiving capstan. In this regard, the at least one shaft may be coaxial with the bobbin. Preferably, the respective sides of the bobbin and the at least one receiving capstan, through which the respective axes pass orthogonally, are in planar alignment with each other. It will be appreciated that the at least one shaft and the at least one receiving capstan may be arranged near to each other.

Optionally, the medicament dispenser comprises at least one indexer that individually indexes the medicament dose portions of the at least one elongate form medicament carrier for dispensing the medicament active. Ideally, the at least one indexer is configured on the medicament dispenser to provide a count of the number of doses remaining. Herein, the at least one indexer is coupled to the aforementioned dispensing mechanism, wherein the at least one indexer indexes a change in count of administered medicament dose portions as the medicament actives are released therefrom by the dispensing mechanism. The at least one indexer enables the user to (a) keep a count of the number of doses remaining, and (b) determine whether the medicament actives have been effectively released from the elongate form medicament carrier and are ready to be taken up, as the number on the at least one indexer changes as soon as the medicament actives have been released by the dispensing mechanism to show the doses remaining.

Notably, the indexer may comprise an arrangement of gears driven by a predefined extent of travel per medicament dose portion. In a simplified implementation of the medicament dispenser, the at least one indexer employs a mechanical counter, typically comprising a series of disks mounted on an axle, with the digits zero to nine marked on edges of the disks, to keep count of the medicament dose portions released from the elongate form medicament carrier. Optionally, the doses remaining are counted in ones, fives or tens, for example. Optionally, the doses remaining are counted in fives. Beneficially, counting in fives makes it easier for printing the numbers on the mechanical counter counting mechanisms. Alternatively, optionally, the at least one indexer is implemented as an electronic counter.

Optionally, a single indexer indexes for the medicament dose portions of one or more elongate form medicament carriers, as the medicament dose portions on the one or more elongate form medicament carriers are always released and administered to the patient simultaneously, therefore the number of administered medicament actives from the one or more elongate form medicament carriers will always be the same.

Alternatively, optionally, plural distinct indexers index the medicament dose portions of one or more elongate form medicament carriers. Specifically, plural (namely, a pair of) distinct indexers are employed in an instance when the medicament dose portions of the first elongate form medicament carrier and the second elongate form medicament carrier are released sequentially. Therefore, since the count of medicament dose portions released from the first and second elongate form medicament carriers are different, distinct indexers are employed to index the corresponding medicament dose portions. Optionally, said plural distinct indexers are mutually coupled. Notably, the plural distinct indexers are coupled such that the count shown by the indexers is in tandem with the medicament dose portions released from the medicament dose portions corresponding to the first and second elongate form medicament carriers.

Alternatively, plural (namely, a pair of) distinct indexers are employed in an instance when the medicament dose portions of the first elongate form medicament carrier and the second elongate form medicament carrier are released simultaneously.

Optionally, the medicament dispenser comprises grip elements configured to flatten the elongate form medicament carrier after dispensing the medicament actives from the medicament dose portions thereof. Specifically, the grip elements operate in a manner similar to a mangle, wherein the grip elements squeeze the medicament dose portions in the used blister elongate sheet together. Alternatively, the grip elements act against a plate and thus squeeze the blister elongate sheet through either side of the plate.

Optionally, any or all components of the dispensing mechanism are drivable by an electronic drive system. Specifically, the medicament dispenser may comprise an electronic drive system housed therein coupled with a power source (such as a battery), wherein the electronic drive system may drive the components such as that of the dispensing mechanism, and optionally, may further drive the rotation of the components such as the at least one receiving capstan and/or the take-up spool.

Optionally, the medicament dispenser additionally comprises an electronic data management system. Optionally, such electronic data management system comprises control instructions for the electronic drive system. Furthermore, optionally, the electronic data management system may store a count of the administered medicament dose portions, details of the medicament actives in the first and second set of medicament dose portions, and timings when the medicament dose portions are to be administered and have been administered.

Optionally, the medicament dispenser comprises a body; a holder, shaped to fit within said body and movable relative to said body; and receivable by said holder, a reload cassette containing one elongate form medicament carrier. Specifically, the reload cassette is insertable into the holder (as shown in FIG. 3) after removal of the existing cassette carrying the existing elongate form medicament carrier. Optionally, the medicament dispenser is in kit of parts form. Specifically, the kit comprises the body, the holder and the reload cassette, wherein the user may load the reload cassette into the holder to engage the elongate form medicament carrier with the medicament dispenser and may start the administration of the medicament dose portions thereafter.

In an example, the elongate form medicament carrier is implemented as a peelable blister strip form medicament carrier and the dispensing mechanism comprises a peeling action for peeling apart the lid elongate sheet from the blister elongate sheet. In an instance when the dispensing mechanism provides the peeling action, the distal end of the lid elongate sheet (that is harnessed on a bobbin) and the distal end of the blister elongate sheet (that is harnessed on a take up spool) progressively separate the further portions of the lid elongate sheet and the blister elongate sheet in diverging paths. The medicament active may then be delivered in an airstream, which is typically provided when the user inhales through the medicament dispenser's nosepiece or mouthpiece. Alternatively, the dispensing mechanism may further comprise a blade arranged between the separated portions of the lid elongate sheet and the blister elongate sheet to progressively separate the further portions thereof.

The present disclosure also relates to the method as described above. Various embodiments and variants disclosed above apply mutatis mutandis to the method.

Optionally, at least one elongate form medicament carrier may be inserted into a medicament dispenser of the disclosure during manufacture. Optionally, the at least one elongate form medicament carrier is assembled into a cartridge (or cassette). The cartridge is designed to insert into a body of the medicament dispenser. The cartridge may comprise at least one feed spool, at least one receiving capstan, a take-up spool, and at least one bobbin. In an exemplary process, a first elongate form medicament carrier is wound onto a first feed spool and a second elongate form medicament carrier is wound onto a second feed spool. A distal end of the lid elongate sheet of the first elongate form medicament carrier is lifted separate from the distal end of the corresponding blister elongate sheet and attached to the circumference of a first bobbin, and similarly, a distal end of the lid elongate sheet of the second elongate form medicament carrier is lifted separate from the distal end of the corresponding blister elongate sheet and attached to the circumference of the second bobbin. Such a process may be carried out on a carriage with spindles that allow the feed spools and bobbins to be positioned for transfer to a unit of the medicament dispenser. The distal ends of the blister elongate sheets of the first and the second elongate form medicament carriers are dragged and harnessed to the take-up spool, specifically, looping the distal end onto a peg of the take-up spool, and arranging the other parts of the first and second elongate form medicament carriers to be fed onto first and second receiving capstans, respectively.

It will be appreciated that assembling the at least one power spring mechanism of the medicament dispenser requires inserting at least one spring into a bobbin such that an inner end of the spring is secured to at least one shaft, wherein at least one shaft is at least partially positioned within the bobbin for securing the inner end, and an outer end of the at least one spring is secured at a side wall of the bobbin. The inner end of the spring may be secured directly or indirectly to the shaft. The outer end of the at least one spring may be secured to a side wall of the bobbin. The at least one bobbin having the spring within it is inserted into the medicament dispenser. Moreover, the inner end of the spring secured to its position by the at least one shaft and the outer end of the at least one spring affixed on the inner side wall of the at least one bobbin enables the pre-defined tension within the spring to be maintained.

Furthermore, the distal end of the lid elongate sheet is harnessed on the circumference of the at least one bobbin having the at least one power spring, and similarly the distal end of the blister elongate sheet is harnessed on the take-up spool. Moreover, the at least one bobbin is rotated to coil a segment (namely, a pre-defined length, or a length within a pre-determined range) of the lid elongate sheet around the at least one bobbin, until the lid elongate sheet is pulled taut. It will be appreciated that said coiling of the segment of the lid elongate sheet around the at least one bobbin prevents the anchor point of the lid elongate sheet (such as the outer end of the at least one spring or any other point on the circumference of the at least one bobbin) from becoming detached by the high force required to peel the lid elongate sheet from the blister elongate sheet during the use of the medicament dispenser. Additionally, said coiling of the segment of the lid elongate sheet around the at least one bobbin ensures that there is no slack in the lid elongate sheet upon first use of the medicament dispenser. Furthermore, during the actuation of the medicament dispenser by the user, the at least one spring unwinds thereby rotating the at least one bobbin which peels a segment of the lid elongate sheet simultaneously from each of the at least one elongate form medicament carrier and exposes the medicament active stored in the medicament dose portions of the elongate form medicament carrier for access into the manifold from when a user inhales through the mouthpiece or nosepiece. In such instance, the at least one bobbin and the take-up spool spools the separated lid elongate sheet and the blister elongate sheet, respectively.

In an implementation of the present disclosure, the medicament dispenser comprises the take-up spool and the pair of bobbins employed to wind up the blister elongate sheet and lid elongate sheet, respectively. In such implementation, the first receiving capstan and the second receiving capstan are driven by a mechanism which coordinates their rotation with the rotation of the take-up spool. Specifically, the mechanism coordinating the rotation ensures the coordinated rotation of the take-up spool and the pair of receiving capstans such that for every actuation of the medicament dispenser, a single distinct medicament dose portion from each of the first and second sets of medicament dose portions is dispensed by peeling apart the lid elongate sheet and the blister elongate sheet.

Optionally, the at least one spring is pre-tensioned for insertion thereof in the at least one bobbin. It will be appreciated that the at least one spring is pre-tensioned during assembly, and then unwinds, thereby reducing the tension in the at least one spring, throughout the use of the medicament dispenser. Moreover, as the at least one spring unwinds the lid elongate sheet is pulled in a direction divergent from the direction of pull of the blister elongate sheet, causing the lid elongate sheet to be peeled from the blister elongate sheet. In such instance, the medicament dose portions sealed between the lid elongate sheet and the blister elongate sheet are exposed to dispense the medicament actives therein, as the medicament dose portions are indexed into position by the user.

Optionally, a unidirectional spring winding rotation of the at least one shaft is retained by at least one of: a ratchet, a clip, a clutch or a stopper.

DETAILED DESCRIPTION OF THE DRAWINGS

Referring to FIGS. 1A, 1B, 1C and 1D, illustrated are schematic views of a power spring mechanism 100, in accordance with an embodiment of the present disclosure. The power spring mechanism 100 comprises a spring 102 having an inner end 102A about which the spring 102 unwinds, and a bobbin 104 which is hollow and cylindrical, an outer end 102B of the spring 102 being secured at a side wall 104A of the bobbin 104. As shown, the spring 102 is ribbon-shaped or coiled-ribbon-shaped, such as to take the form of a spiral spring when assembled in the power spring mechanism 100. Moreover, the spring 102 is pre-tensioned for insertion thereof in the bobbin 104. Furthermore, the spring 102 is arranged to unwind about the rotational axis of the bobbin 104.

Moreover, the power spring mechanism 100 comprises a shaft 106 at least partially positioned within the bobbin 104 for securing the inner end 102A of the spring 102. As shown, the shaft 106 is coaxial with the bobbin 104.

FIG. 1A illustrates a perspective view of the power spring mechanism 100. As shown, the spring 102 as supplied is assembled into the bobbin 104, wherein the inner end 102A of the spring 102 is secured directly or indirectly to the shaft 106. The coils of the spring 102 are in their most expanded state within the bobbin 104, as this is the assembly position before tensioning.

Figure 1B:
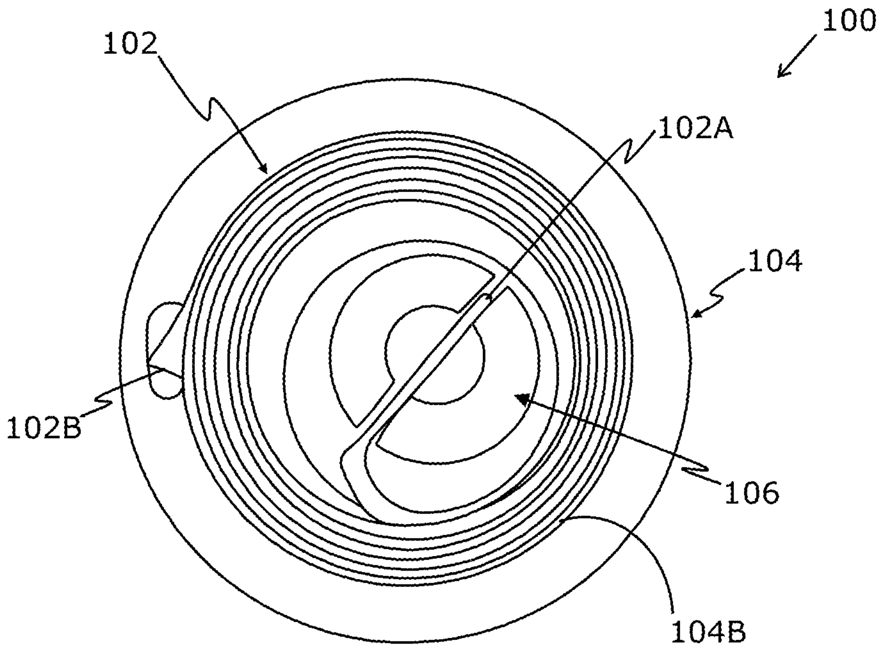

FIG. 1B illustrates a top view of the power spring mechanism 100, i.e., the same state of tension as in FIG. 1A. As shown, the spring 102 rests against an inside face 104B of the bobbin 104. It will be appreciated that the spring 102 is already in a tensioned state in the bobbin 104. Notably, the spring 102 has tension but is stable and unable to release its stored energy, because there is no space for the coils of the spring 102 to expand into.

Figure 1C:
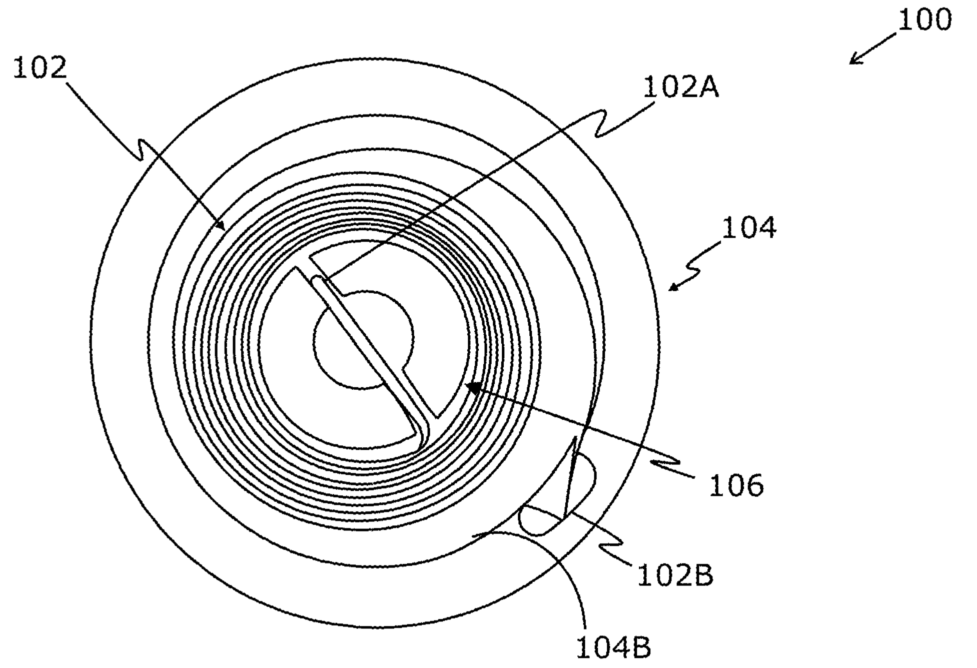

FIG. 1C illustrates a top view of power spring mechanism 100, after almost fully tensioning. The spring 102 tensioning corresponds to the medicament dose portion registered with a manifold of a medicament dispenser being dose portion number 'zero', i.e., before the first dose is actuated. As shown, the spring 102 is mostly tightly coiled around the shaft 106.

Figure 1D:
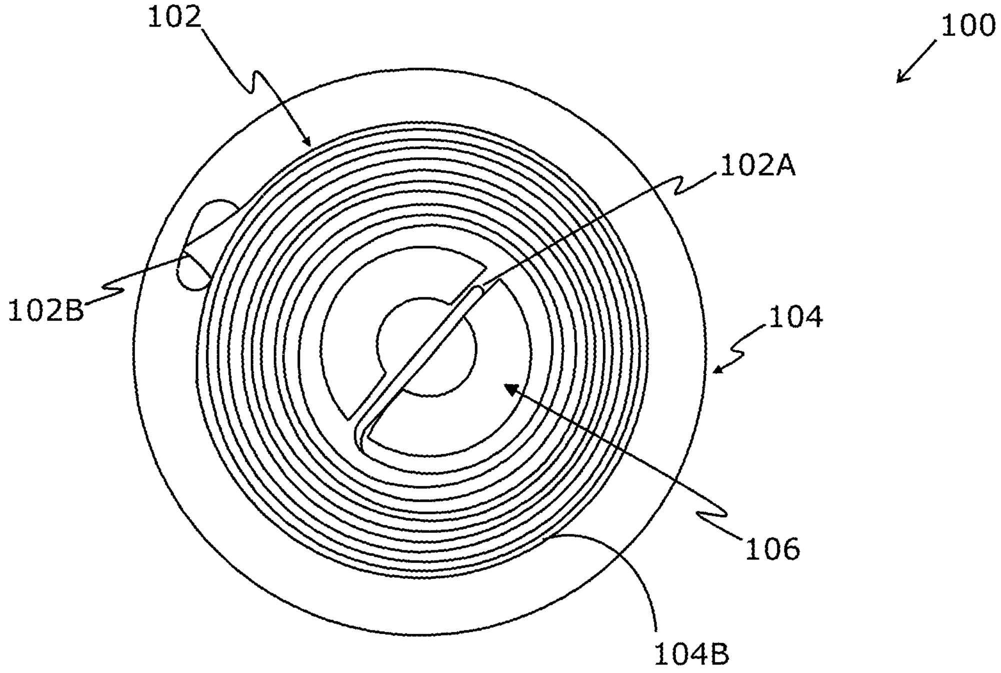

FIG. 1D illustrates a top view of the power spring mechanism 100. As shown, the spring 102 has a residual tension when the medicament dose portion registered with the manifold is dose portion number 'thirty', i.e., the last medicament dose portion has been registered with the manifold. As shown, the spring 102 coils are not fully returned to their rest position, i.e., against the inside face 104B of the bobbin 104, thus indicating a residual tension in the power spring mechanism 100. By using part of the available tension in the spring 102 to dispense all doses (before the spring reaches the condition shown in FIGS. 1A and 1B), the torque applied through life does not tail off towards the last dose.

Figure 1E:
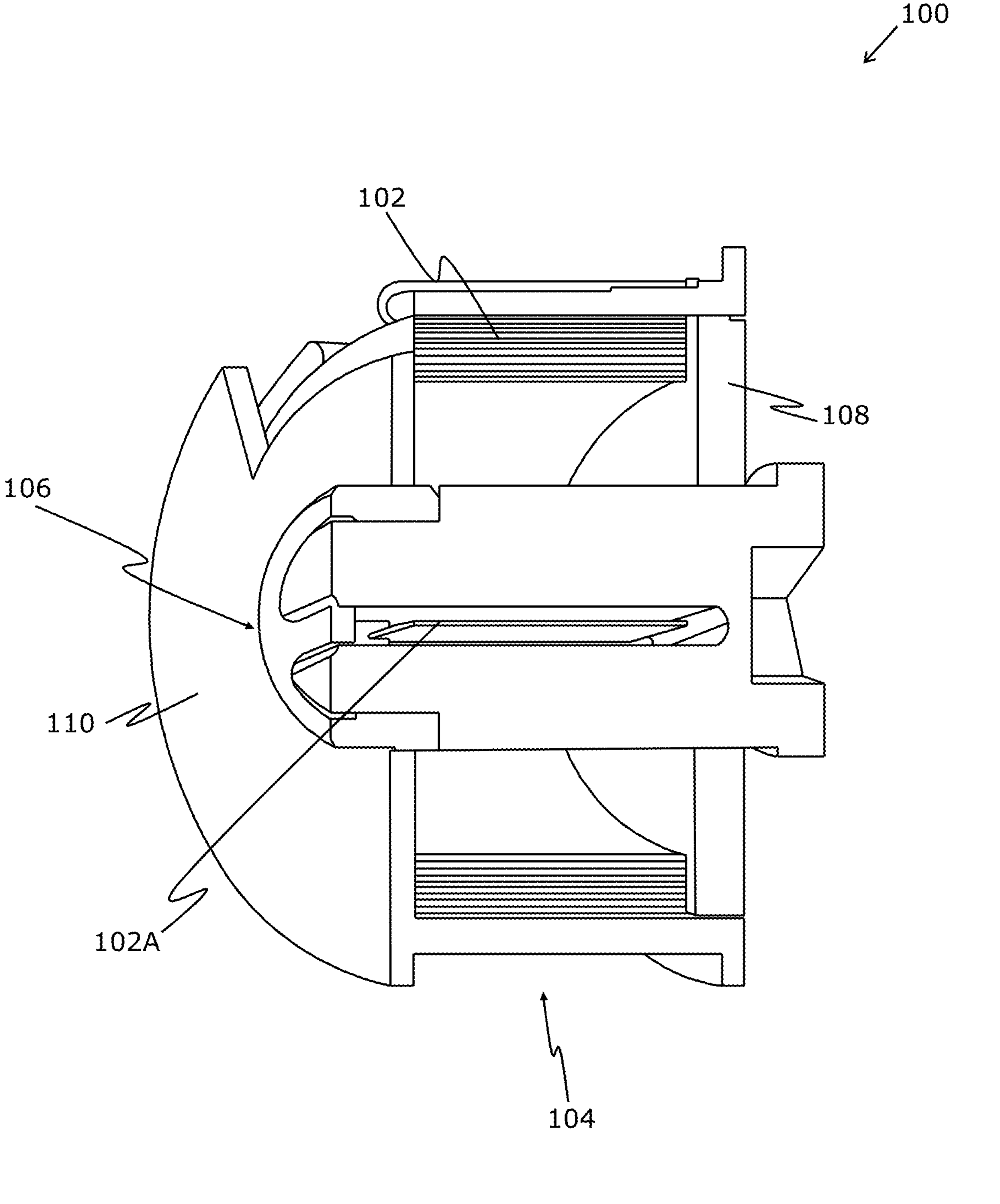
FIG. 1E is a sectional schematic view of a power spring mechanism, in accordance with an embodiment of the present disclosure.

Referring to FIG. 1E, illustrated is a sectional schematic view of the power spring mechanism 100, in accordance with an embodiment of the present disclosure. As shown, the shaft 106 secures the inner end 102A of the spring 102. Moreover, the shaft 106 is mounted in the medicament dispenser in a manner to prevent movement of the shaft 106 when the medicament dispenser is in use. As shown, the shaft 106 is retained for ease of rotation by retaining means 108, 110. As shown, the retaining means 108 and 110 are walls of the holder 300 as explained in FIGS. 3A and 3B below.

Figure 1F:
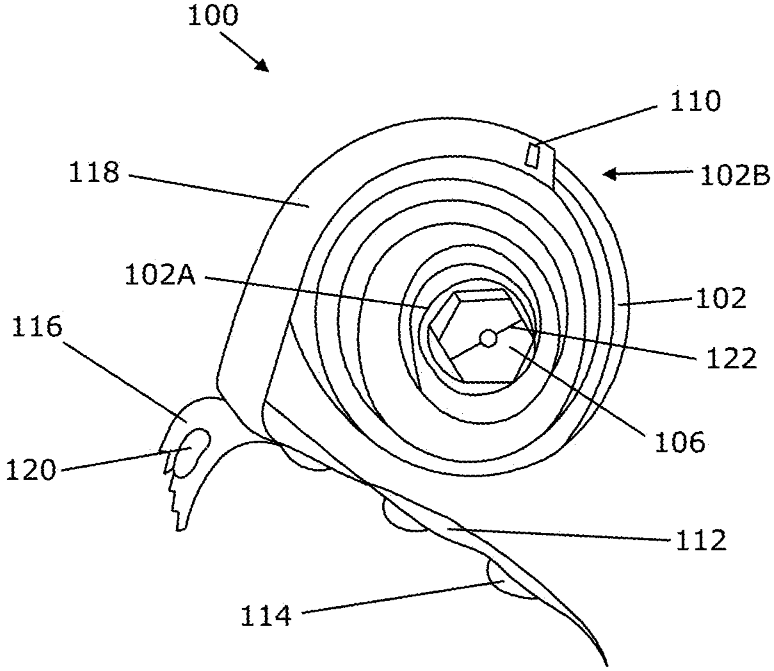
FIG. 1F is a schematic view of another embodiment of a power spring mechanism in accordance with an embodiment of the present disclosure.

FIG. 1F shows a schematic view of a power spring mechanism in accordance with another embodiment of the present disclosure. The power spring mechanism 100 comprises a spring 102, coiled spirally, having an inner end 102A about which the spring 102 unwinds and which is attached to a shaft 106 through slits 122 therein. An outer end 102B of the spring 102 is secured to the distal end of a lid elongate sheet. In a suitable securing structure, the elongate sheet is provided with a slot into which a widened part 110 of the spring is inserted.

The elongate sheet 112 is shown at a stage before it is peeled apart where it has sealed blisters 114. After peeling to provide a base elongate sheet 116 and a lid elongate sheet 118, the base elongate sheet has open blisters 120.

The shaft 106 is shown with a hexagonal end, and a similar hexagonal end is provided on the rear side of the power spring mechanism. The power spring mechanism is inserted into a medicament dispenser, which may be provided with a ratchet mechanism, such as shown in FIG. 1G, that engages the hexagonal end of the shaft, allowing it to rotate in only one direction relative to the medicament dispenser, in FIG. 1F it is clockwise.

Figure 1G:
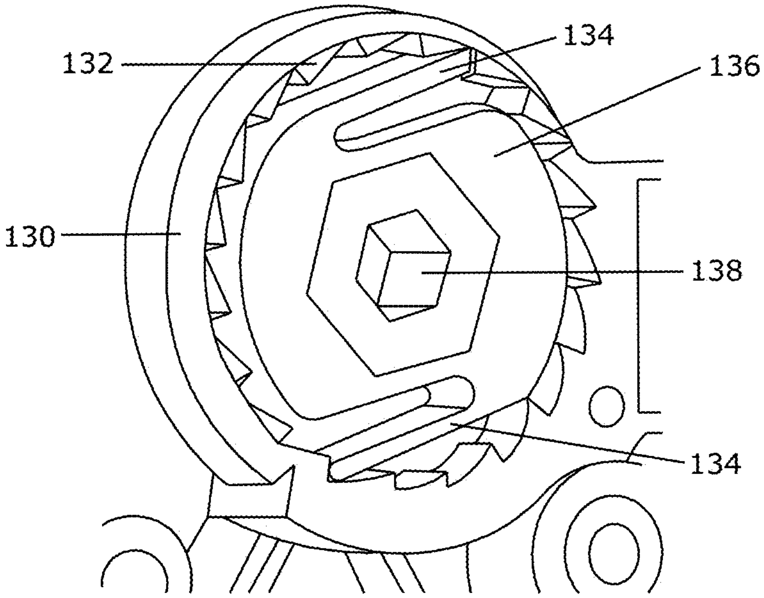
FIG. 1G is a schematic view of a ratchet mechanism, suitable for incorporation into the medicament dispenser.

FIG. 1G is a view of the ratchet mechanism from the opposite side with respect to the power spring mechanism, and hence designed to rotate anticlockwise. A ring extension 130 of the medicament dispenser has teeth 132 arranged circumferentially on an inner surface of the ring. Each tooth has a long surface and a short surface. A ratchet pawl carrier 136 is provided with a mounting comprising a hexagonal orifice 138. The ratchet pawl carrier 136 has a pair of pawls 134, that are directed at the short surfaces of two diametrically opposite teeth. When the pawl carrier is rotated in the allowed direction, the pawls ride over the long surfaces of the teeth.

In one method of assembly, the power spring mechanism is attached to the distal end of an elongate sheet. It is then mounted into the medicament dispenser such that a hexagonal end of the shaft is engaged in the hexagonal orifice. Other non-circular cooperating shapes for the end of the shaft and the orifice are possible, e.g., rectangles, cross shapes. The spring is then tensioned by turning the other end of the hexagonal shaft, until a prescribed torque is reached. Once tensioned, no further adjustments of the shaft are made in use of the medicament dispenser.

Figure 2A:
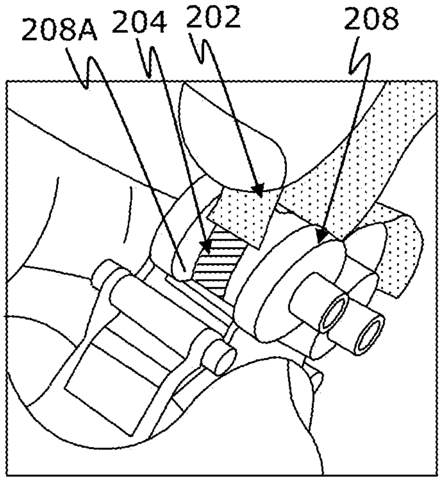
FIGS. 2A, 2B, 2C and 2D are schematic illustrations of steps of anchoring and tensioning a distal end of the lid elongate sheet by or near to a circumference of a bobbin, in accordance with an embodiment of the present disclosure.
Figure 2B:
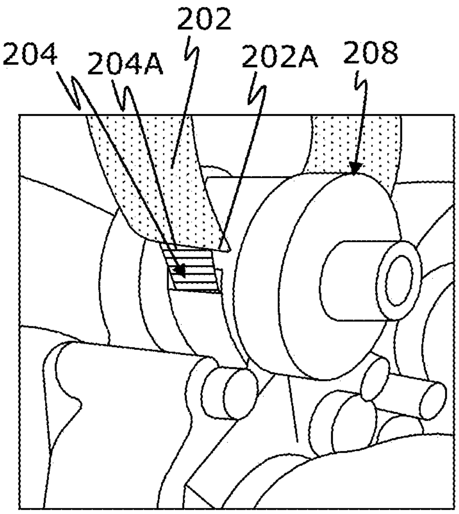
Figure 2C:
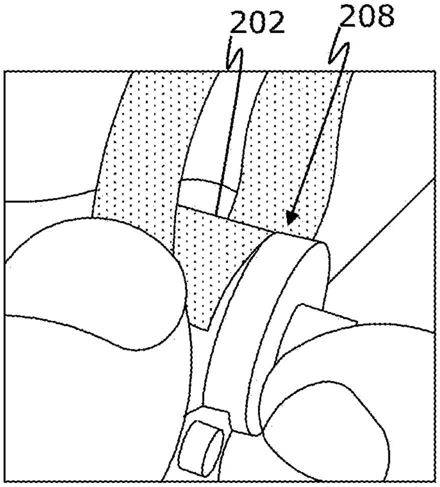
Figure 2D:
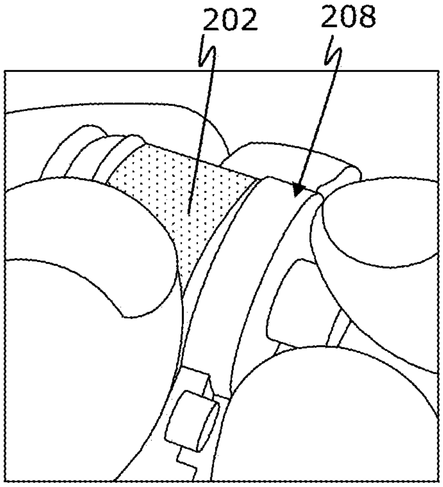

Referring to FIGS. 2A, 2B, 2C and 2D, illustrated are schematic illustrations of steps 200 of anchoring and tensioning a distal end 202A of the lid elongate sheet 202 by or near to a circumference 208A of the bobbin 208, in accordance with an embodiment of the present disclosure. These FIGs. show hand assembly, and show the fingers and thumb of the person performing the assembly operation. As shown in FIGS. 2A and 2B, the distal end 202A of the lid elongate sheet 202 is anchored to the outer end 204A of the spring 204 that is secured at the side wall 208A of the bobbin 208. It will be appreciated that at this stage the distal end of the blister elongate sheet (not shown) is harnessed on a take-up spool (not shown). Moreover, as shown in FIGS. 2C and 2D, the bobbin 208 is rotated to coil a segment (namely, a pre-defined length) of the lid elongate sheet 202 around the bobbin 208, until the lid elongate sheet 202 is pulled taut. Furthermore, during subsequent actuation of the medicament dispenser by a user, the spring 204 unwinds thereby rotating the bobbin 208 to peel further segments of the lid elongate sheet 202 from corresponding segments of the blister elongate sheet simultaneously to dispense medicament active stored in a medicament dose portions of the elongate form medicament carrier (not shown).

Figure 3A:
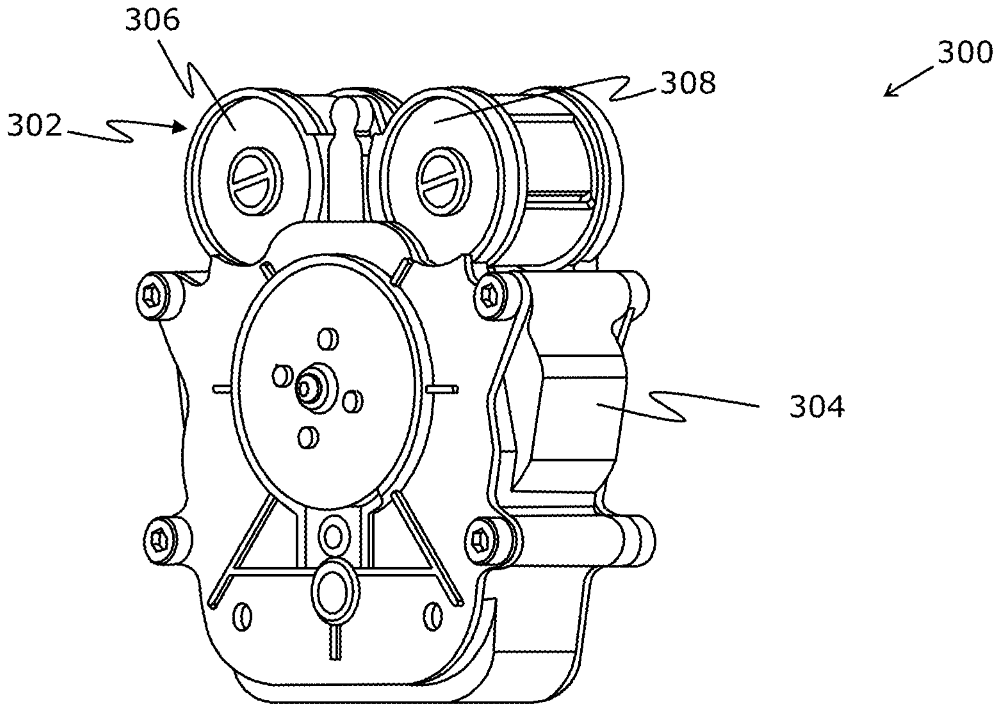
FIGS. 3A and 3B, are external views of opposite sides of a holder of a medicament dispenser, in accordance with an embodiment of the present disclosure.
Figure 3B:
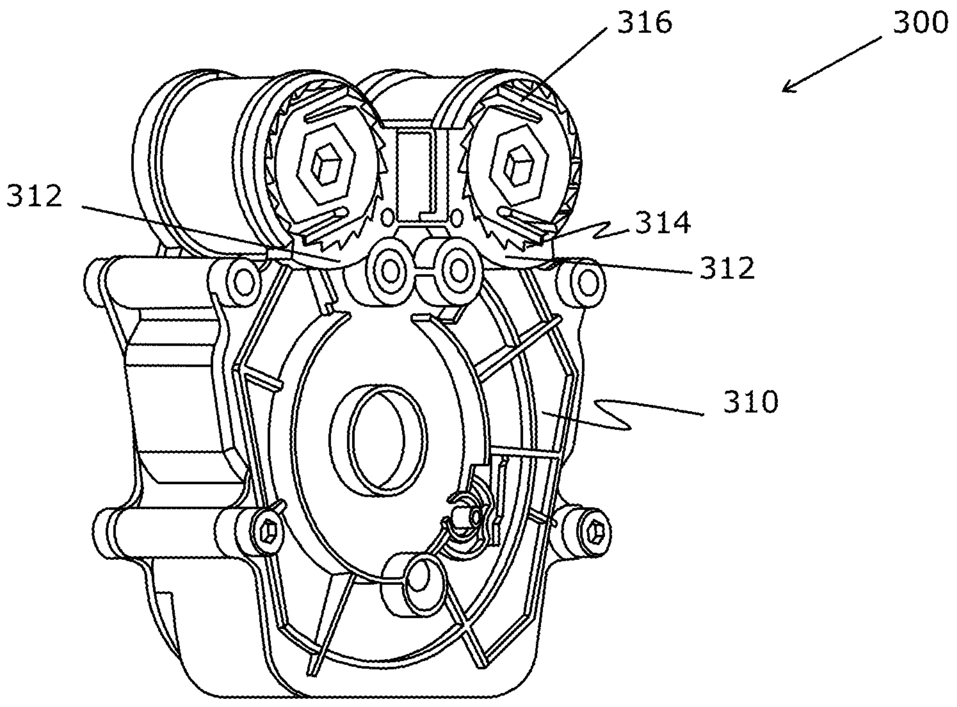

Referring to FIGS. 3A and 3B, illustrated are external views of opposite sides of a holder 300 of a medicament dispenser, in accordance with an embodiment of the present disclosure. The holder 300 holds the at least one elongate form medicament carrier. The holder 300 is housed within an outer housing (not shown) of the medicament dispenser. The holder 300 has a casing part 302, which has walls 304 that surround the elongate form medicament carrier and a pair of drum ends 306, 308 for a pair of power spring mechanisms, in a unitary moulding. The drum ends 306, 308 provide mountings for a second end of each shaft, such as the shaft 106 as explained in FIG. 1, of the pair of power spring mechanisms. The holder 300 has a lid part 310, which encloses the elongate form medicament carrier by abutting the edges of the walls of the casing part 302. The lid part 310 is moulded to include a pair of rings 312 of inwardly-directed ratchet teeth 314 for engaging corresponding pawls 316 that are attached to corresponding shafts.

Figure 4:
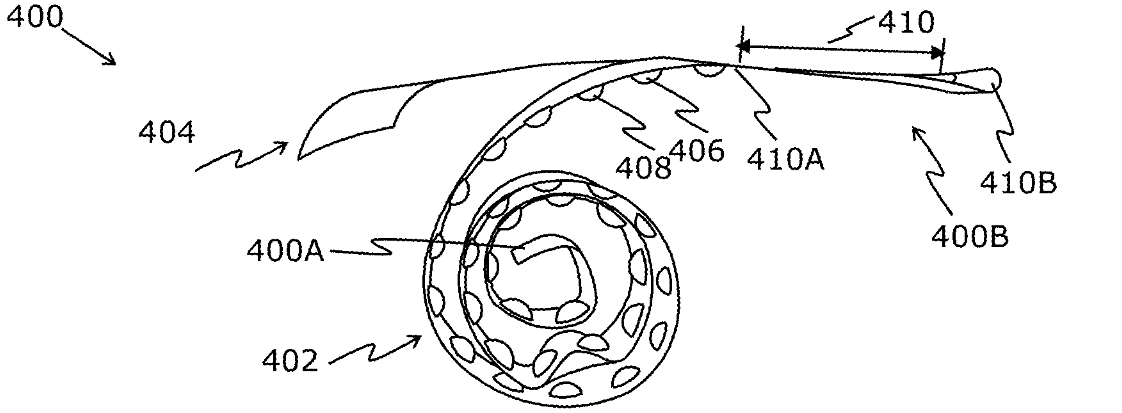
FIG. 4 is a perspective view of an elongate form medicament carrier, in accordance with an embodiment of the present disclosure.

Referring to FIG. 4, illustrated is a perspective view of an elongate form medicament carrier 400, in accordance with an embodiment of the present disclosure. The elongate form medicament carrier 400 has a proximal end 400A, a distal end 400B, and a blister elongate sheet 402 and a lid elongate sheet 404 enclosing multiple distinct medicament dose portions, depicted as the exemplary medicament dose portions 406, and 408, therebetween. As shown, the multiple distinct medicament dose portions are uniformly spaced. Notably, the distal end 400B of the elongate form medicament carrier 400 does not comprise the multiple distinct medicament dose portions, and appears as a flat length of foil 410 having a first end region 410A and a second end region 410B. Optionally, the second end region 410B is a looped end.

It may be understood by a person skilled in the art that FIG. 4 illustrates one simplified implementations of the elongate form medicament carrier 400, for the sake of clarity, which should not unduly limit the scope of the claims herein. The person skilled in the art will recognize many variations, alternatives, and modifications of embodiments of the present disclosure.

Figure 5:
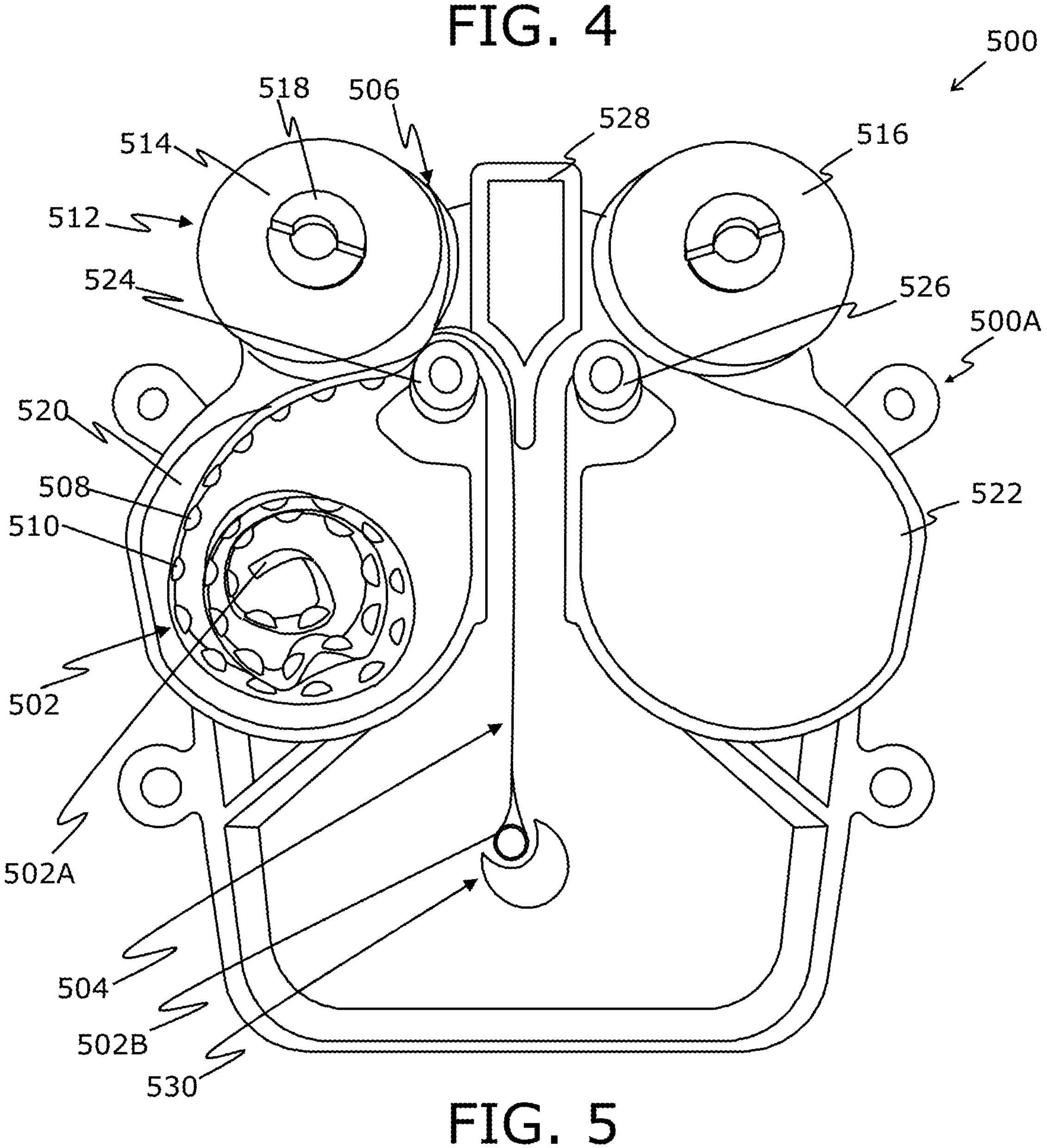
FIG. 5 is a sectional view of part of a medicament dispenser, in accordance with an embodiment of the present disclosure.

Referring to FIG. 5, illustrated is a sectional view of part of a medicament dispenser 500, in accordance with an embodiment of the present disclosure. Shown is the inner side of the first part 500A of the medicament dispenser 500. The medicament dispenser 500 holds an elongate form medicament carrier 502, similar to the elongate form medicament carrier 400 explained in FIG. 4. The elongate form medicament carrier 502 has a proximal end 502A, a distal end 502B, and a blister elongate sheet 504 and a lid elongate sheet 506 enclosing multiple distinct medicament dose portions, depicted as the exemplary medicament dose portions 508, and 510, therebetween. Moreover, the medicament dispenser 500 has a dispensing mechanism which is adapted to operate, upon each actuation of the medicament dispenser 500, to dispense a medicament active from a medicament dose portion of the elongate form medicament carrier 502. The dispensing mechanism comprises a power spring mechanism 512 (such as the power spring mechanism 100 explained in FIG. 1) for winding the lid elongate sheet 506. Moreover, the power spring mechanism comprises a spring (not shown) having an inner end about which the spring unwinds, and an outer end secured at a side wall of a bobbin, depicted as (514 and 516), wherein the bobbin 514 (and 516) is a hollow cylindrical bobbin. Furthermore, the power spring mechanism 512 comprises a shaft 518 at least partially positioned within the bobbin 514 (and 516) for securing the inner end of the spring. Moreover, a pre-defined unwinding of the spring spools a segment of the lid elongate sheet 506 peeled from a corresponding segment of the blister elongate sheet 504, to be tensioned by the bobbin 514 (and 516).

The dispensing mechanism further comprises at least one receiving portion, depicted as the receiving portion 520 and 522, for receiving the at least one elongate form medicament carrier, such as the elongate form medicament carrier 502, having multiple distinct medicament dose portions. Moreover, the receiving portion comprises at least one receiving capstan, depicted as the receiving capstan 524 and 526, for receiving the medicament dose portions of the at least one elongate form medicament carrier; and a manifold 528, associated with at least one receiving capstan, for dispensing the medicament active from the medicament dose portion of the at least one elongate form medicament carrier. The dispensing mechanism further comprises a take-up spool 530 for holding a distal end 502B of the blister elongate sheet 504.

Figure 6:
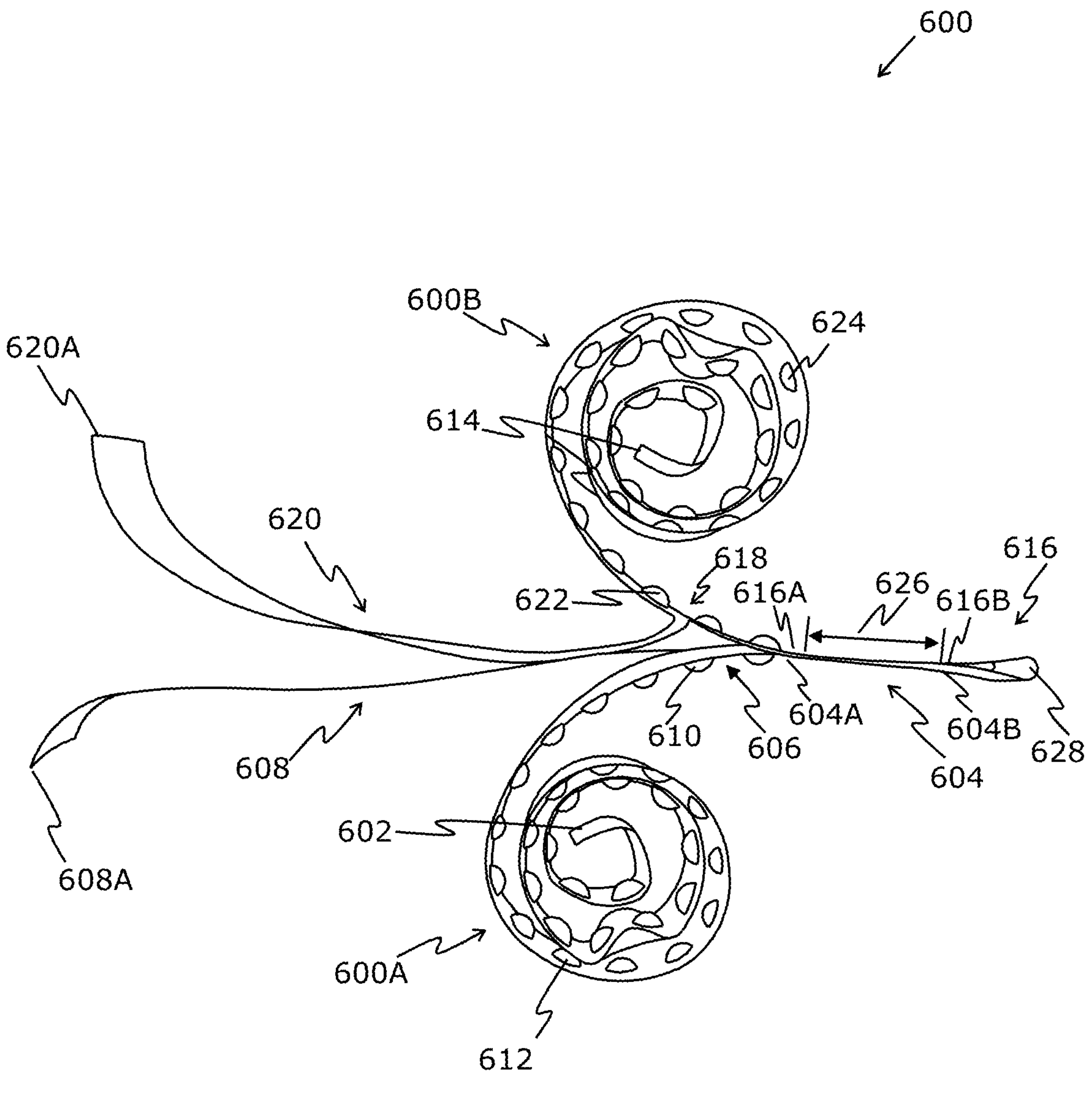
FIG. 6 is a perspective view of an elongate form medicament carrier, in accordance with another embodiment of the present disclosure.

Referring to FIG. 6, illustrated is a perspective view of an elongate form medicament carrier 600, in accordance with an embodiment of the present disclosure. The elongate form medicament carrier 600 is implemented as an elongate strip form medicament carrier with a two-portion elongate form medicament carrier comprising a first portion 600A and a second portion 600B. The first portion 600A has a proximal end 602, a distal end 604, and a blister elongate sheet 606 and a lid elongate sheet 608 enclosing multiple distinct medicament dose portions, depicted as the exemplary medicament dose portions 610 and 612, therebetween. Similarly, the second portion 600B has a proximal end 614, a distal end 616, and a blister elongate sheet 618 and a lid elongate sheet 620 enclosing multiple distinct medicament dose portions, depicted as the exemplary medicament dose portions 622 and 624, therebetween. As shown, the multiple distinct medicament dose portions are uniformly spaced. Moreover, the each of the distal ends 604 and 616 of the first portion 600A and the second portion 600B, respectively, do not comprise the multiple distinct medicament dose portions, and appear as a flat length of foil having a first end region 604A and 616A and a second end region 604B and 616B, respectively. Furthermore, the length of foils of both the first portion 600A and the second portion 600B are combined together face-to-face to form a unified length 626 and the second end regions 604B and 616B thereof are combined (or connected) to form a common loop 628. Moreover, the unified length 626 comprises only the length of foil of the blister elongate sheets 606 and 618 of the first portion 600A and the second portion 600B, respectively, while the corresponding segments of the lid elongate sheets 608 and 620 of the first portion 600A and the second portion 600B, respectively, are peeled therefrom and harnessed to the corresponding bobbins (not shown). Furthermore, the first portion 600A and the second portion 600B appear to be forked at the respective first end regions 604A and 616A thereof. In such arrangement, the common loop 628 brings the two-portion elongate form medicament carrier into a folded configuration such that the lid elongate sheet 608 corresponding to the first portion 600A faces the lid elongate sheet 620 corresponding to the second portion 600B. Moreover, the lid elongate sheets 608 and 620 have distal ends 608A and 620A, respectively, wherein the distal ends 608A and 620A are not secured to the blister elongate sheets 606 and 618 and are later harnessed to the corresponding bobbins.

Figure 7:
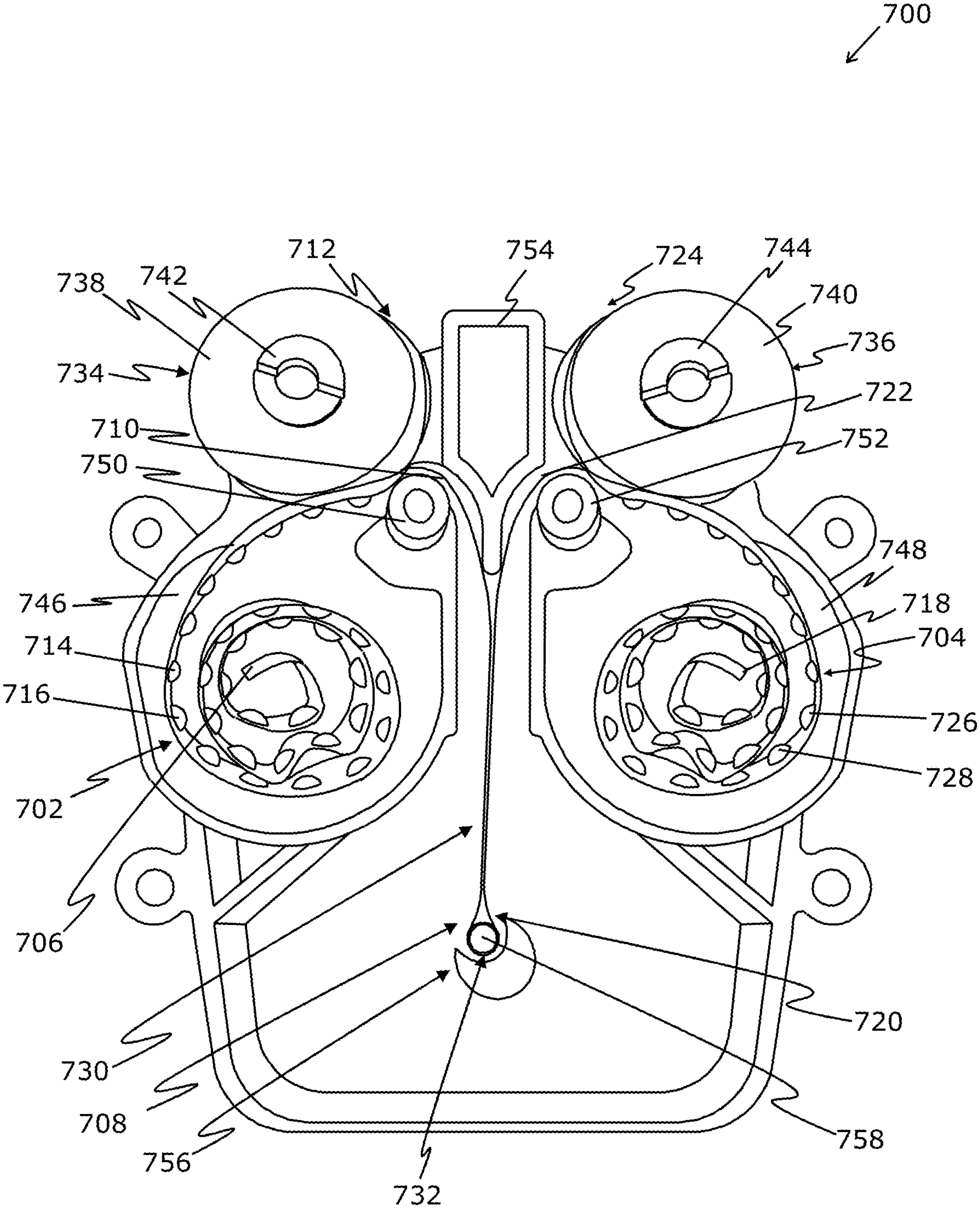
FIGS. 7 and 8 are sectional views of part of a medicament dispenser, in accordance with another embodiment of the present disclosure.
Figure 8:
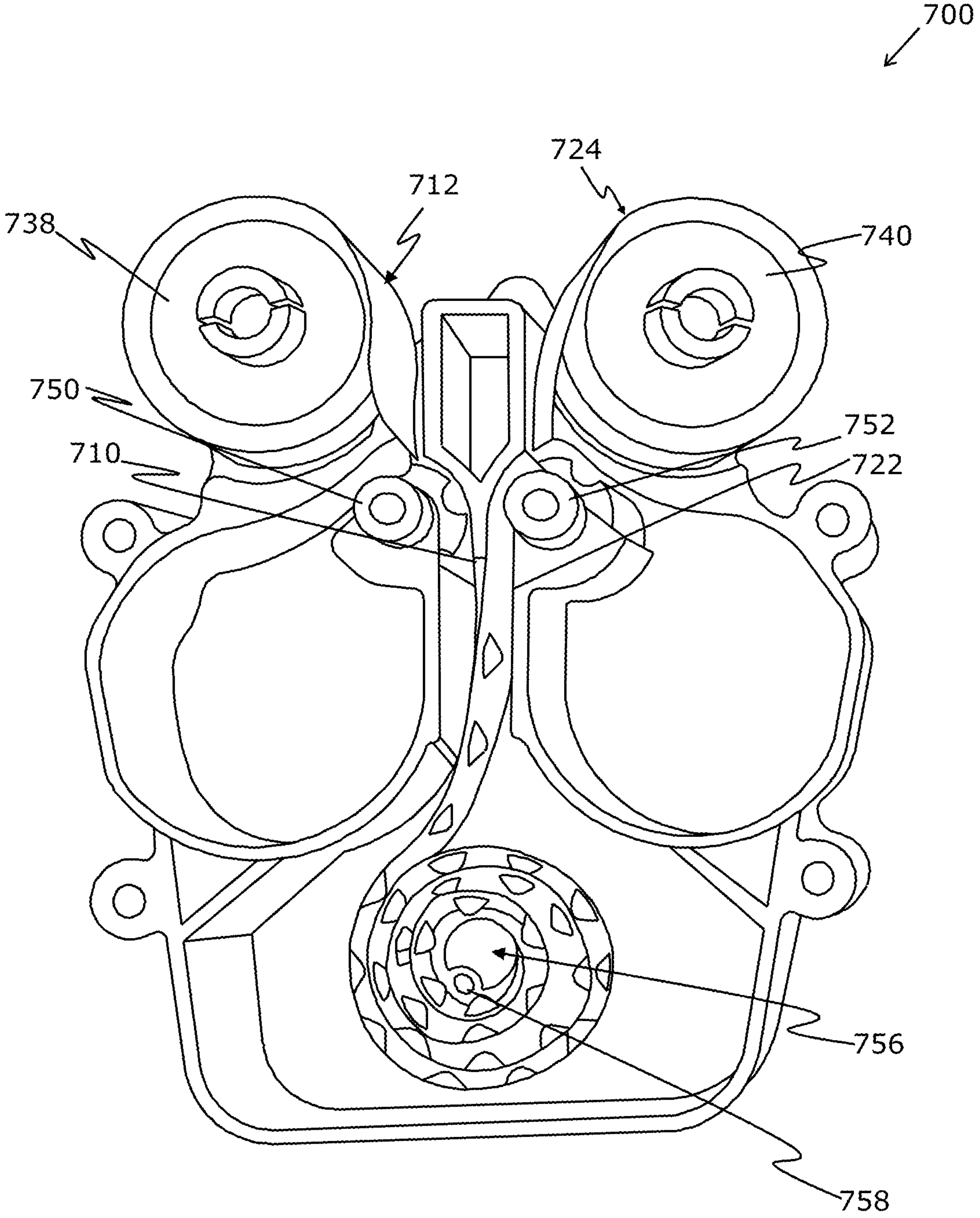

Referring to FIGS. 7 and 8, illustrated are sectional views of part of a medicament dispenser 700, in accordance with another embodiment of the present disclosure. The medicament dispenser 700 holds at least one elongate form medicament carrier (such as the elongate form medicament carrier explained in FIG. 6), comprising a first portion 702 and a second portion 704 (such as the first portion 600A and a second portion 600B explained in FIG. 6). The first portion 702 has a proximal end 706, a distal end 708, and a blister elongate sheet 710 and a lid elongate sheet 712 enclosing multiple distinct medicament dose portions, depicted as the exemplary medicament dose portions 714 and 716, therebetween. Similarly, the second portion 704 has a proximal end 718, a distal end 720, and a blister elongate sheet 722 and a lid elongate sheet 724 enclosing multiple distinct medicament dose portions, depicted as the exemplary medicament dose portions 726 and 728, therebetween. Moreover, a certain length of the blister elongate sheets 710 and 722 are combined together face-to-face to form a unified length 730 wherein the corresponding lid elongate sheets 712 and 724 are peeled apart from said length of the blister elongate sheets 710 and 722. The unified length 730 ends in a loop 732 formed by combining (or connecting) distal ends 708 and 720.

Moreover, the medicament dispenser 700 has a dispensing mechanism which is adapted to operate, upon each actuation of the medicament dispenser 700, to dispense a medicament active from a medicament dose portion of the at least one elongate form medicament carrier. The dispensing mechanism comprises at least one power spring mechanism 734 and 736 (such as the power spring mechanism 100 explained in FIGS. 1A-1E) for winding the lid elongate sheet 712 and 724. Moreover, the at least one power spring mechanism 734 and 736 comprises at least one spring (such as the spring 102 explained in FIGS. 1A-1E) having an inner end about which the at least one spring unwinds, and an outer end secured at a side wall of a bobbin, such as the bobbins 738 and 740, wherein the bobbin is a hollow cylindrical bobbin, and at least one shaft, such as the shafts 742 and 744, at least partially positioned within the bobbin 738 and 740, respectively, for securing the inner end of the at least one spring, wherein a pre-defined unwinding of the at least one spring spools a segment of the lid elongate sheet 712 and 724 peeled from a corresponding segment of the blister elongate sheet 710 and 722, to be tensioned by the bobbin, such as the bobbin 738 and 740.

The dispensing mechanism further comprises at least one receiving portion, such as the receiving portions 746 and 748, for receiving the at least one elongate form medicament carrier 702 and 704 respectively. The receiving portion 746 and 748 comprises at least one receiving capstan, such as the receiving capstans 750 and 752, for receiving the medicament dose portions of the at least one elongate form medicament carrier 702 and 704 respectively; and a manifold 754, associated with at least one receiving capstan 750 and 752, for dispensing the medicament active from the medicament dose portion of the at least one elongate form medicament carrier 702 and 704 respectively. The dispensing mechanism further comprises a take-up spool 756 for holding distal ends 708 and 720 of the blister elongate sheet 710 and 722, that together form the loop 732. Moreover, the take-up spool 756 comprises a peg 758 that secures the loop 732.

As shown in FIG. 8, as the take-up spool 756 is rotated, starting with the loop 732 (see FIG. 7), the take-up spool 756 continues to wind the used portions of the blister elongate sheet 710 and 722 thereon after dispensing medicament actives from the medicament dose portions. During the said process, as the receiving capstans 750 and 752 are rotated, starting with the distal ends (not shown) of the lid elongate sheet 712 and 724 the pair of bobbins 738 and 740 continue to wind thereon the portions of the lid elongate sheet 712 and 724 corresponding to the used portions of the blister elongate sheet 710 and 722 after dispensing medicament active from the medicament dose portions.

Modifications to embodiments of the present disclosure described in the foregoing are possible without departing from the scope of the present disclosure as defined by the accompanying claims. Expressions such as “including”, “comprising”, “incorporating”, “have” and “is” used to describe and claim the present disclosure are intended to be construed in a non-exclusive manner, namely allowing for items, components or elements not explicitly described also to be present. Reference to the singular is also to be construed to relate to the plural.

The invention claimed is:

1. A medicament dispenser for holding at least one elongate form medicament carrier, the at least one elongate form medicament carrier having a proximal end, a distal end, and a blister elongate sheet and a lid elongate sheet enclosing multiple distinct medicament dose portions therebetween, the medicament dispenser having a dispensing mechanism which is adapted to operate, upon each actuation of the medicament dispenser, to dispense a medicament active from a medicament dose portion of the multiple distinct medicament dose portions of the at least one elongate form medicament carrier, said mechanism comprising:

at least one power spring mechanism for winding the lid elongate sheet, wherein the at least one power spring mechanism comprises:

at least one spring having an inner end about which the at least one spring unwinds, wherein the at least one spring is a coil-ribbon-shaped spring and an outer end of the coil-ribbon-shaped spring is configured to directly attached to a distal end of the lid elongate sheet; and at least one shaft at which the inner end of the at least one spring is secured, wherein the power spring mechanism tensions and peels a segment of the lid elongate sheet from a corresponding segment of the blister elongate sheet upon each actuation of the medicament dispenser.

2. The medicament dispenser according to claim 1, wherein the dispensing mechanism further comprises a bobbin which is hollow and cylindrical, the outer end of the at least one spring being secured at a side wall of the bobbin, the at least one shaft being at least partially positioned within the bobbin.

3. The medicament dispenser according to claim 1, wherein the dispensing mechanism further comprises:

at least one receiving portion for receiving the at least one elongate form medicament carrier having multiple distinct medicament dose portions, the receiving portion comprising:

at least one receiving capstan for receiving the medicament dose portions of the at least one elongate form medicament carrier; and a manifold, associated with at least one receiving capstan, for dispensing the medicament active from each of the medicament dose portions of the at least one elongate form medicament carrier; and a take-up spool for holding a distal end of the blister elongate sheet.

4. The medicament dispenser according to claim 3, wherein the take-up spool comprises a peg for securing the distal end of the blister elongate sheet.

5. The medicament dispenser according to claim 3, wherein the dispensing mechanism is configured to drive the at least one receiving capstan and the take-up spool with gears.

6. The medicament dispenser according to claim 3, wherein the manifold has an opening for inhalation of the dispensed medicament active by a user.

7. The medicament dispenser according to claim 3, wherein the at least one shaft is arranged on an axis parallel to the at least one receiving capstan.

8. The medicament dispenser according to claim 1, wherein the power spring mechanism peels the segment of the lid elongate sheet corresponding to an at least one receiving capstan receiving the medicament dose portion.

9. The medicament dispenser according to claim 1, wherein the shaft is coaxial with the bobbin.

10. The medicament dispenser according to claim 1, wherein the shaft is mounted in the medicament dispenser in a manner to prevent movement of the shaft when the medicament dispenser is in use.

11. The medicament dispenser according to claim 1, wherein the bobbin has a rotational axis and the at least one spring is arranged to unwind about the rotational axis of the bobbin.

12. The medicament dispenser according to claim 1, wherein the spring is fabricated from any one or more of: a metal, an alloy of metal, a plastic, a paper or a rubber.

13. The medicament dispenser according to claim 1, wherein the medicament dispenser comprises at least one indexer that individually indexes the medicament dose portions of the at least one elongate form medicament carrier for dispensing the medicament active.

14. The medicament dispenser according to claim 1, wherein the at least one spring peels the segment of the lid elongate sheet from the corresponding segment of the blister elongate sheet.

15. A method of assembling the medicament dispenser according to claim 1, the method comprising:

inserting the at least one elongate form medicament carrier into at least one receiving portion of the medicament dispenser, the at least one elongate form medicament carrier having the proximal end, the distal end, and the blister elongate sheet and the lid elongate sheet enclosing multiple distinct medicament dose portions therebetween;

anchoring a distal end of the blister elongate sheet to a take-up spool of the medicament dispenser;

assembling the at least one power spring mechanism of the medicament dispenser, such that the inner end of the spring is secured to at least one shaft;

anchoring the distal end of the lid elongate sheet by or near to the outer end of the spring;

receiving at least one medicament dose portions of the at least one elongate form medicament carrier on the at least one receiving capstan; and tensioning the lid elongate sheet and the blister elongate sheet on the at least one power spring mechanism and the take-up spool respectively.

16. The method according to claim 15, wherein the assembling the at least one power spring mechanism of the medicament dispenser comprises inserting the at least one spring into a bobbin, wherein the bobbin is hollow and cylindrical, such that the at least one shaft is at least partially positioned within the bobbin for securing the inner end of the at least one spring, and the outer end of the at least one spring is secured at a side wall of the bobbin, such that the anchoring of the distal end of the lid elongate sheet is by or near to a circumference of the bobbin.

17. The method according to claim 15, wherein the at least one spring is pre-tensioned for insertion in the at least one bobbin.

18. The method according to claim 15, wherein a unidirectional spring winding rotation of the at least one shaft is retained by at least one of: a ratchet, a clip, a clutch or a stopper.

* * * * *